(12) United States Patent
Jones et al.

(10) Patent No.: US 6,329,208 B1
(45) Date of Patent: Dec. 11, 2001

(54) METHODS FOR DETERMINING GLUCONEOGENESIS, ANAPLEUROSIS AND PYRUVATE RECYCLING

(75) Inventors: John G. Jones; A. Dean Sherry; F. M. H. Jeffrey, all of Dallas; G. Larry Cottam, Richardson; Craig. R. Malloy, Dallas, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/118,338

(22) Filed: Jul. 16, 1998

Related U.S. Application Data

(60) Provisional application No. 60/052,081, filed on Jul. 16, 1997.

(51) Int. Cl.[7] .......................... G01N 33/48; G01N 33/50; G01N 33/58; G01N 33/66

(52) U.S. Cl. .......................... 436/173; 424/9.3; 424/9.35; 435/4; 435/29; 435/30; 435/35; 436/56; 436/63; 436/94; 436/95; 436/127; 436/128; 436/129

(58) Field of Search ...................... 424/9.3, 1.81, 424/9.35; 435/4, 14, 29, 30, 35; 436/56, 63, 94, 95, 127, 128, 129, 173

(56) References Cited

U.S. PATENT DOCUMENTS

| | | | |
|---|---|---|---|
| 5,324,636 | * 6/1994 | Bartos et al. | 435/35 |
| 5,413,017 | * 5/1995 | Malloy et al. | 435/35 |
| 5,439,803 | * 8/1995 | Ross et al. | 435/14 |
| 5,597,548 | * 1/1997 | Sherry et al. | 424/9.3 |
| 5,722,346 | * 3/1998 | Tremblay et al. | 119/230 |
| 5,767,141 | * 6/1998 | Schubert et al. | 514/393 |

OTHER PUBLICATIONS

Y. Y. Lin et al, Anal. Biochem. Mar. 1993, 209, 267–273.*
J. G. Jones et al, Biochemistry Nov. 1993, 32, 12240–12244.*
J. Katz et al, J. Biol. Chem. Dec. 1993, 268, 25509–25521.*
A. D. Sherry et al, Magn. Reson. Med. Apr. 1994, 31, 374–379.*
J. A. Vogt et al, Am. J. Physiol. Jun. 1994, 266, E1012–E1022.*
A. Lapidot et al, J. Biol. Chem. Nov. 1994, 268, 27198–27208.*
C. A. Fernandez et al, J. Biol. Chem. Apr. 1995, 270, 10037–10042.*
B. R. Landau et al, Am. J. Physiol. Jan. 1995, 269, E18–E26.*
S. F. Previs et al, J. Biol. Chem. Aug. 1995, 270, 19806–19815.*
P. J. Reeds et al, Eur. J. Pediatr, 1997, 156 (Suppl. 1) S50–S58.*
Anousie et al., "Inhibition of pyruvate cycling in mouse livers perfused with $[1,2,3-^{13}C]$propionate,"*ISMRM*, Van Couver, Apr. 12–18, 1997.
Carvalho et al., "Oxidation of substrates highly enriched in $^{13}C$: influence on detection of long range $^{13}C-^{13}C$ coupling in glutamate," *ISMRM*, Van Couver, Apr. 12–18, 1997.

(List continued on next page.)

*Primary Examiner*—Arlen Soderquist
(74) *Attorney, Agent, or Firm*—Fulbright & Jaworski

(57) ABSTRACT

Simple equations that relate glucose, glutamate, glucuronate, and phenylacetylglutamine $^{13}C$ NMR multiplet areas to gluconeogenesis and pyruvate recycling during metabolism of $[1,2,3-^{13}C_3]$propionate are presented. This indicates that a direct measure of gluconeogenesis, pyruvate recycling, and anaplerosis may be obtained from a single $^{13}C$ NMR spectrum of suitably prepared blood or urine samples collected after oral administration of enriched propionate, acetaminophen, and phenylacetate.

31 Claims, 9 Drawing Sheets

OTHER PUBLICATIONS

Cline et al., "$^{13}$C–nuclear magnetic resonance spectroscopy studies of hepatic glucose metabolism in normal subjects and subjects with insulin–dependent diabetes mellitus,"–*J. Clin. Invest.*, 94:2369–2376, 1994.

Corkey et al., "Regulation of the branched chain α–Ketoacid pathway in liver," *J. Biol. Chem.*, 257:9668–9676, 1982.

Des Rosiers et al., "Isotopomer analysis of citric acid cycle and gluconeogenesis in rat liver," *J. Biol. Chem.*, 270:10027–10036, 1995.

Jeffrey et al., "$^{13}$C isotopomer model for estimation of anaplerotic substrate oxidation *via* acetyl–CoA,"*Am J. Physiol.*, 271:E788–E799, 1996.

Jones and Titheradge, "Measurement of metabolic fluxes through pyruvate kinase, phosphoenolpyruvate carboxykinase, pyruvate dehydrogenase, and pyruvate carboxylase in hepatocytes of different acinar origin," *Arch. Biochem. Biophys.*, 326:202–206, 1996.

Jones, Cottam, Sherry, Malloy, "$^{13}$C NMR isotopomer measurements of gluconeogenesis and oxaloacetate recycling in perfused in perfused organs supplied with [U–$^{13}$C]propionate," ISMRM, Van Couver, Apr. 12–18, 1997.

Jones et al., "A method for obtaining $^{13}$C isotopomer populations in $^{13}$C–enriched glucose," *Anal. Bioch.*, 217:148–152, 1994.

Jones et al., "Measurement of hepatic glucose output, krebs cycle, and gluconeogenic fluxes by NMR analysis of a single plasma glucose sample," *Anal. Bioch.*, 263:39–45, 1998.

Jones et al., "Measurement of gluconeogenesis and pyruvate recycling in the rat liver: a simple analysis of glucose and glumate isotopomers during metabolism of [1,2,3–$^{13}$C$_3$] propionate," *FEBS Lett.*, 412:131–137, 1997.

Landua et. al., "Contributions of gluconeogenesis to glucose production in the fasted state," *J. Clin. Invest.*, 98:378–385, 1996.

Malloy et al., "Contribution of various substrates to total citric acid cycle flux and anaplerosis as determined by $^{13}$C isotopomer analysis and O$_2$ consumption in the heart," *MAGMA*, 4:35–46, 1996.

Malloy et al., "Analysis of tricarboxylic acid cycle of the heart using $^{13}$C isotope isomers," *Am. J. Physiol.*, 259:H987–H995, 1990.

Malloy et al., "Evaluation of carbon flux and substrate selection through alternate pathways involving the citric acid cycle of the heart by $^{13}$C NMR spectroscopy," *J. Biol. Chem.*, 263:6964–6971, 1988.

Malloy et. al., "Carbon flux through citric acid cycle pathways in perfused heart by $^{13}$C NMR spectroscopy," *FEBS. Lett.*, 212:58–62, 1987.

Sherry et.al., "Orientation–conserved transfer of symmetric krebs cycle intermediates in mammalian tissue," *Biochemistry*, 33:6268–6275, 1994.

Sherry and Malloy, "Isotopic methods for probing organization of cellular metabolism," *Cell Biochem. Func.*, 14:259–268, 1996.

Szczepaniak et. al., "Oxidation of acetate in rabbit skeletal muscle: detection by $^{13}$C NMR spectroscopy in vitro," *Magn. Reson. Med.*, 36:451–457, 1996.

\* cited by examiner

GLUTAMATE 1 2 3 4 5

C3S=12%

C3D=46%

C3T=42%

CALCULATED
SPECTRUM

OBSERVED
SPECTRUM

METHODS FOR DETERMINING GLUCONEOGENESIS, ANAPLEUROSIS AND PYRUVATE RECYCLING

This application claims priority from U.S. Provisional Patent Application No. 60/052,081 filed Jul. 16, 1997.

The government owns rights in the present invention pursuant to grant numbers RR02584 and HL34557 from the National Institute of Health.

BACKGROUND OF THE INVENTION

1. Field of the Invention

The invention relates to convenient and efficient methods of assay and diagnosis of metabolic states, particularly gluconeogenesis, pyruvate flux and anapleurosis.

2. Description of Related Art

Current methods for the measurement of gluconeogenesis in humans require exposure to radioactive materials. Unfortunately, this feature precludes almost any quantitative studies of these pathways in patients. The development of $^{13}C$ NMR for clinical applications is very attractive because of its convenience and the dramatic improvement in metabolic detail which it can provide. Although direct in vivo NMR spectroscopy is the most exciting application for $^{13}C$ tracer studies, it is unlikely that appropriate whole-body systems will be widely available any time soon for clinical research. On the other hand, analytical NMR spectrometers suitable for $^{13}C$ NMR studies of human blood or urine are already in place in every medical school in this country.

Measurement of hepatic gluconeogenesis using both $^{13}C$ and $^{14}C$-labeled glucose is by now a well-developed approach and had been successfully applied in both animals and humans. However, measurements of absolute anaplerotic fluxes have been largely restricted to perfused organs and tissues and the methods cannot be performed in vivo. Since only gluconeogenesis can currently be measured noninvasively, a necessary simplification is to assume that gluconeogenesis is equal to anapleurosis. The penalty for this assumption is that the total anaplerotic flux is underestimated to an unknown degree, and the allocation of anaplerotic carbons between gluconeogenesis and the other biosynthetic pathways is not known.

There is widespread interest in measurement of flux through gluconeogenesis in animals and humans with the goal of a better understanding of dietary and hormonal regulation of fluxes through all associated pathways. Numerous techniques have been used for such measurements, including GC-mass spectrometry (Katz et al., 1993; Katz, 1985; Tayek and Katz, 1996) NMR (Cohen, 1981; Cohen, 1987; Cohen, et al. 1981), and radiotracers (Strisower et al., 1952; Landau et al., 1993). One key control point that connects these two pathways is the interconversion of PEP and pyruvate, catalyzed in the forward direction by pyruvate kinase and in the reverse direction by the combined action of pyruvate carboxylase and phosphoenolpyruvate carboxykinase. Many early studies of gluconeogenesis detected excess cycling of three carbon units through this metabolic intersection. This process, often referred to as pyruvate recycling on an excess substrate cycle, has been detected in studies of isolated hepatocytes (Clark et al., 1973; Jones and Titheradge, 1996), perfused livers (Friedman et al., 1971), and in rats and humans (Magnusson et al., 1990; Petersen et al., 1994).

Most early metabolic models have relied on measurements of isotope enrichment in two or more sites of various product molecules. In prior metabolic studies of pathways associated with the Krebs citric acid cycle, the detection of $^{13}C$-$^{13}C$ spin-spin NMR couplings in product molecules has been demonstrated. This approach, which is referred to as $^{13}C$ isotopomer analysis, can in some cases provide more information about isotope labeling patterns than other tracer methods. Recently, the analysis of propionate metabolism in the isolated heart under conditions where the pathway succinyl-CoA→pyruvate→acetyl-CoA was significant (Jeffrey et al., 1996) was reported. In contrast to entry of labeled acetyl-CoA and scrambling of this label in cycle reactions, this metabolic condition yields a series of nonlinear equations, which in general are difficult to solve analytically. Although the Newton-Raphson procedure is well known (Press et al., 1988), the complexity of the equations in the comprehensive model obscures some simple and helpful relations between the $^{13}C$ NMR spectrum and metabolic state. One such condition occurs during hepatic metabolism of $[1,2,3-^{13}C]$propionate.

SUMMARY

The present invention seeks to overcome the aforesaid and other drawbacks by providing a method allowing gluconeogenesis and total anapleurosis to be measured independently, but simultaneously, in a non-invasive manner. This method is unique because it does not require radioactive tracers and can be easily transferred to the clinical environment for studies of abnormalities in glucose metabolism and hepatic synthetic function. The method allows routine and convenient analysis of gluconeogenesis and other pathways intersecting the citric acid cycle of the liver under almost any clinical circumstance. The basic approach is applicable to animal models and to humans.

Simple interpretations of the $^{13}C$ NMR spectra of glucose, glutamate, glucuronide and phenylacetylglutamine are presented in terms of gluconeogenesis and pyruvate recycling. The methods are demonstrated in isolated perfused rat livers, in samples collected from rats after intragastric versus intravenous administration of propionate, and in humans after oral ingestion of propionate, phenylacetate, and acetaminophen. The data demonstrate that gluconeogenesis and pyruvate recycling can be measured in a single $^{13}C$ NMR spectrum of glucose obtained from blood samples or of glucuronide or phenylacetylglutamine obtained from urine samples after oral administration of $[1,2,3-^{13}C]$ propionate, phenylacetate, and acetaminophen. The simple processing protocols for both blood and urine are well within the capability of a standard medical analytical laboratory. The disclosed methods will be particularly useful in studying and assessing liver damage, such as caused by diabetes, sepsis, cirrhosis and other diseases that affect liver function. Additionally, the methods may be useful in assessing the effect of liver damage caused by trauma.

Figure 1:
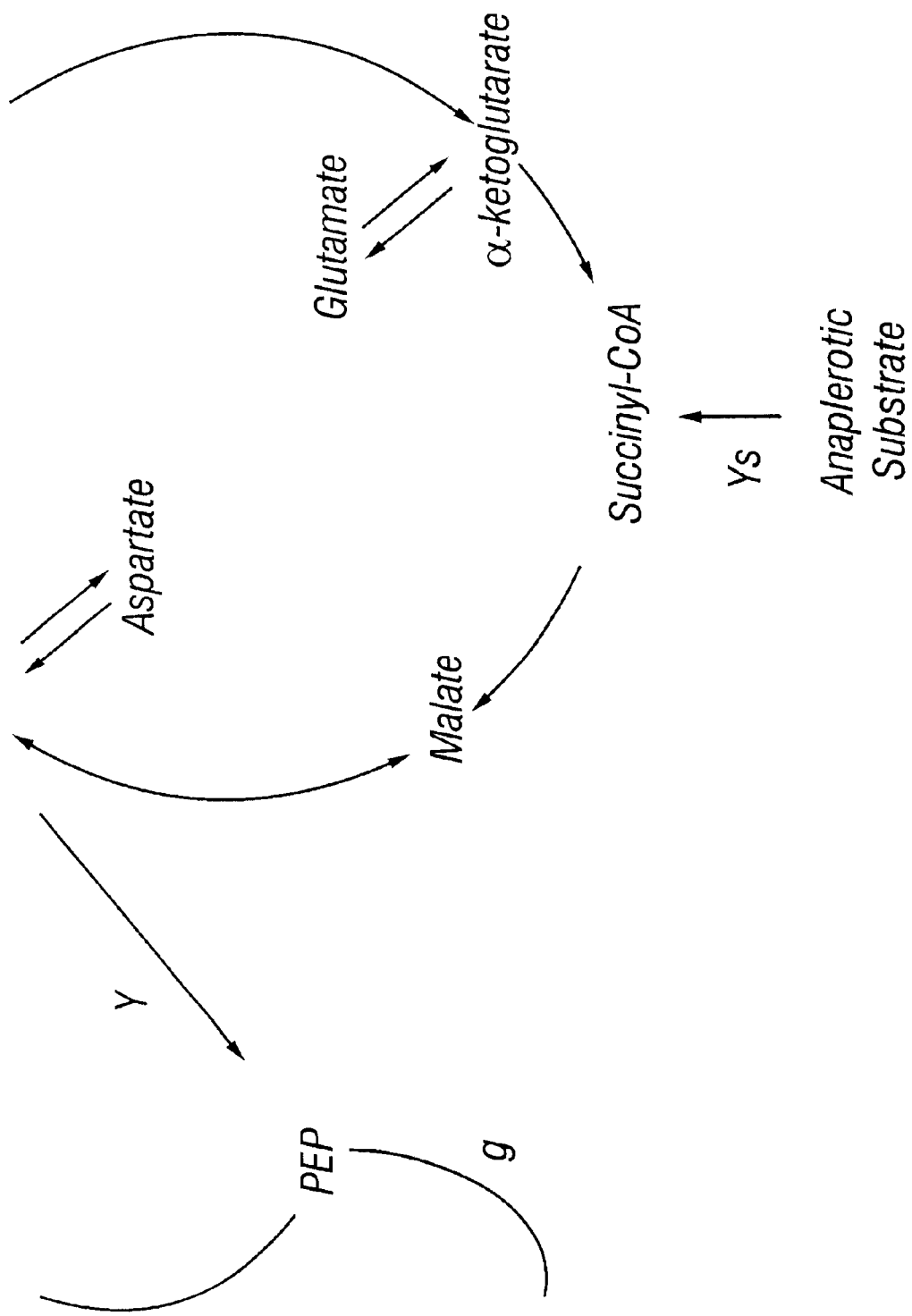
FIG. 1 shows the metabolic model. All fluxes are relative to flux through citrate synthase (CS). Other abbreviations: PDH, pyruvate dehydrogenase complex; LDH, lactate dehydrogenase; PK, pyruvate kinase; g, gluconeogenesis: $y_s$, flux through the combined anaplerotic pathways feeding succinyl-CoA, including propionate carboxylation; $y_{PC}$ flux through pyruvate carboxylase.
Figure 2A:
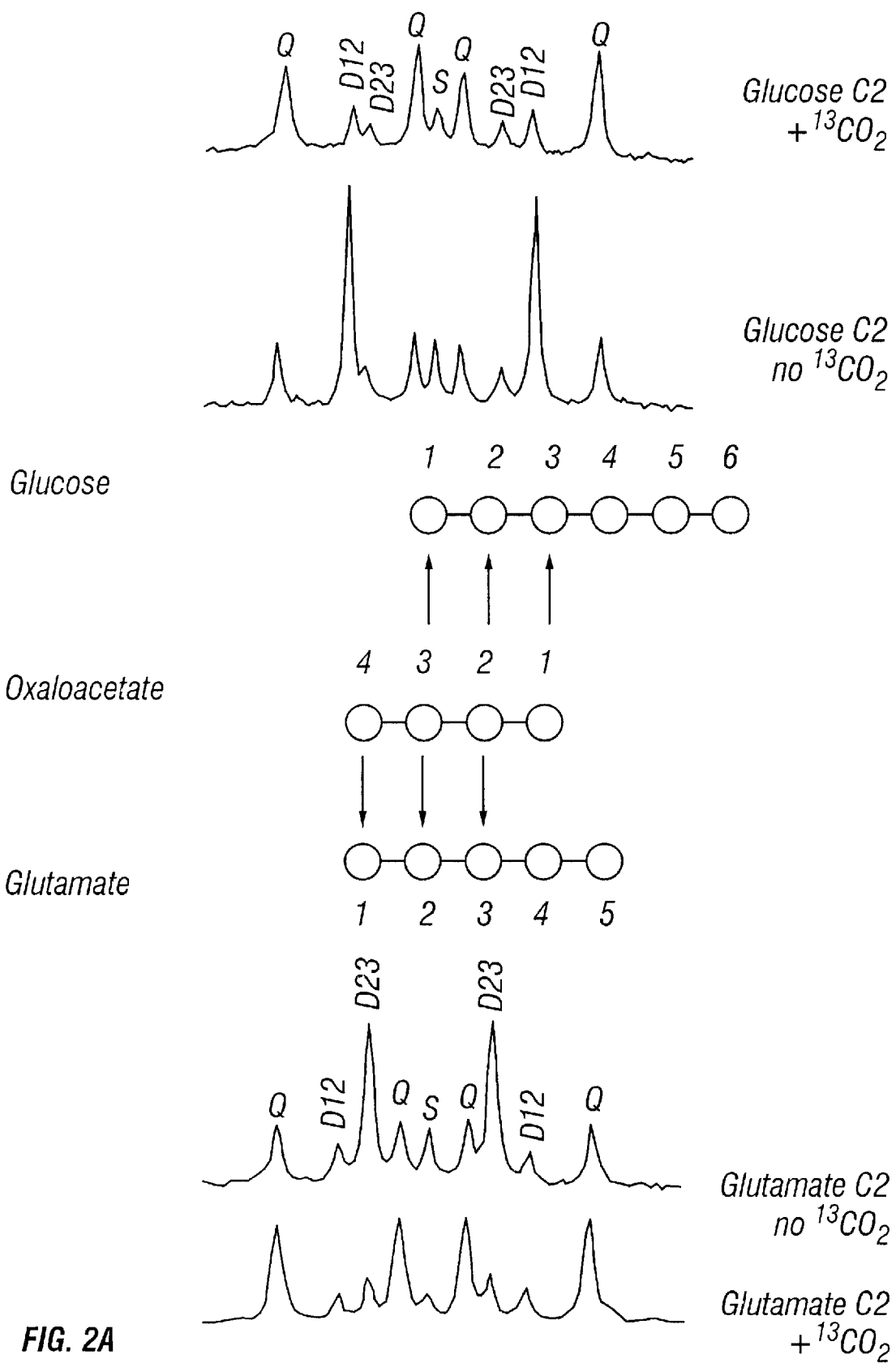
FIG. 2(a) shows the relation of $^{13}C$ enrichment in oxaloacetate to glutamate and glucose, and the effects of $^{13}CO_2$ on the proton decoupled $^{13}C$ NMR spectra of carbon 2 from gluconate and glutamate. Multiplets are defined in the text. The spectra labeled "no $^{13}CO_2$" were obtained from a liver supplied with [1,2,3-$^{13}$C]propionate plus unlabeled substrates as described in the text. The spectra labeled "÷$^{13}$C" were obtained under the same conditions except that $^{13}CO_2$ was present in high concentration. Since $^{13}CO_2$ would increase $^{13}$C enrichment in OAA carbon 1 or carbon 4, the quartet (Q) increased in the C2 resonance of both glucose and gluconate.
Figure 2B:
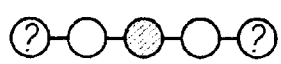
FIG. 2(b) illustrates the singlet, doublet, and triplet components of a typical glutamate C3 resonance multiplet. The observed multiplet is that of the C3 resonance from a heart perfused with 2.5 mM [2-$^{13}$C] acetate and 2.5 mM pyruvate. As shown, the contribution of the singlet (C3S), the doublet (C3D), and the triplet (C3T) to the total multiplet area is 12, 46, and 42% respectively.
Figure 2B:
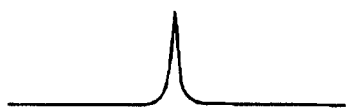
Figure 2B:
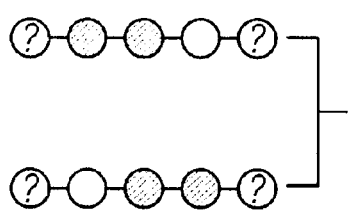
Figure 2B:
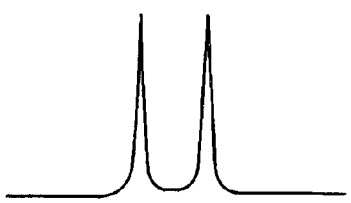
Figure 2B:
Figure 2B:
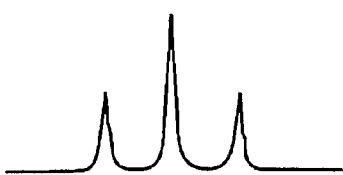
Figure 2B:
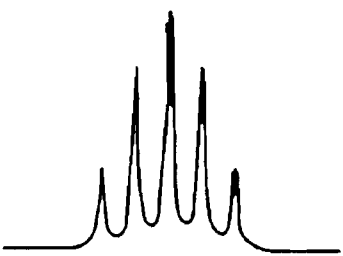
Figure 2B:
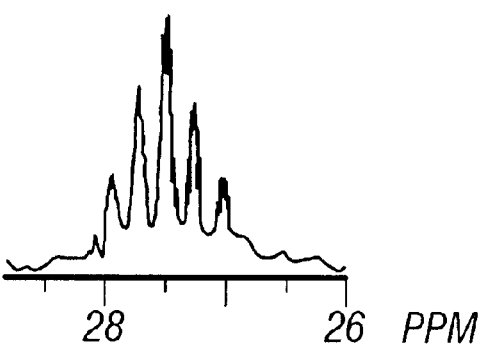

For the H5β inset, S refers to a singlet resonance of carbon 5; D56 to a doublet resonance arising from coupling between carbons 5 and 6; D45 to a doublet resonance arising from coupling between carbons 4 and 5; Q to a quartet arising from coupling of carbon 5 with carbons 4 and 6.

DETAILED DESCRIPTION OF PREFERRED EMBODIMENTS

The present invention discloses methods to directly measure relative gluconeogenesis and pyruvate recycling rates in the liver based upon an analysis of $^{13}$C NMR spectra of various products of the hepatic metabolism of [U-$^{13}$C] propionate. The methods have been demonstrated with glucose and glutamate samples obtained from biopsy of rat livers, glucose samples obtained from human blood samples, and glucuronate and phenylacetylglutamine samples obtained from human urine samples. Glucose, glutamate, glucuronate and phenylacetylglutamine analyses were chosen for analysis for several reasons. Glutamate (assumed equivalent to glutamine) can be sampled noninvasively in humans by chemical biopsy (Magnusson, et al., 1990), glucose is readily obtainable from blood samples, and glucuronate and phenylacetylglutamine are readily obtainable from urine samples. Also, these metabolites share a common metabolic intermediate in OAA so questions about compartmentation of OAA may be addressed.

Propionate was chosen as the source of the $^{13}$C label for several reasons. Unlike other gluconeogenic substrates such as lactate, pyruvate and alanine, propionate enters the citric acid cycle by a single and irreversible anaplerotic pathway (Ando et al., 1972). Propionate is also efficiently extracted from the circulation (Fafournoux et al., 1985) and is avidly utilized as an anaplerotic substrate by the liver (Jones et al. 1994; Sherry et al., 1994).

Uniformly enriched propionate was chosen over a tracer enriched in a single carbon position so that all metabolic products would contain multiplets rather than singlets. This becomes an important factor whenever $^{13}$C enrichment of metabolic products is low and one is uncertain whether natural abundance $^{13}$C signal contributes significantly to a spectrum (Lapidot and Gopher, 1994 ). Since the glutamate C2, gluconate (glucose) C2, glucuronate C5β, and phenylacetylglutamine C2 multiplet analyses do not contain spin singlet terms, the disclosed method provides a reliable measure of gluconeogenesis and pyruvate recycling regardless of $^{13}$C enrichment levels. The only limitation is that the enrichment must be sufficient so that the C2 doublet and quartet components are not overwhelmed by a large singlet component due to natural abundance $^{13}$C.

A second advantage of [U-$^{13}$C]propionate is illustrated by the work of Landau et al. (1993) who were unable to obtain a measure of pyruvate cycling using either [2-$^{14}$C]- or [3-$^{14}$C]propionate. They reported that gluconeogenic flux was two or more times Krebs cycle flux and that less than one-twenty-fifth of any pyruvate derived from propionate reentered the citric acid cycle as acetyl-CoA. These results are consistent with the inventors' values measured in both the perfused and in vivo rat liver.

The key components of the hepatic network for propionate metabolism are anaplerotic inflow (y), oxaloacetate-pyruvate recycling (pk), net gluconeogenic outflow (g) and citrate synthase flux as shown in FIG. 1. Anaplerotic inflow is the total influx of both new and recycled C4 units into the oxaloacetate pool. Oxaloacetate-pyruvate recycling flux is the combined activities of all pathways that convert oxaloacetate to pyruvate then back to oxaloacetate. These include OAA→PEP→PYR→OAA (which the inventors define as the pyruvate kinase pathway); OAA→MAL→PYR→OAA (which the inventors define as the malic enzyme pathway); and the Cori and glucose-alanine cycles, where hepatic glucose (synthesized from oxaloacetate) is metabolized by peripheral tissues to pyruvate, lactate and alanine which are then recycled in the liver to glucose via oxaloacetate. Gluconeogenic flux is the difference between total anaplerotic inflow and total oxaloacetate-pyruvate recycling, and represents the net production of carbon from the citric acid cycle. While anaplerotic carbons can leave the citric acid cycle through pathways other than gluconeogenesis (for example as aspartate and glutamate), it is generally assumed that gluconeogenesis accounts for the bulk of the total anaplerotic carbon outflow in liver. The distribution of C2 glucose isotopomers in this study is sensitive to the relative fluxes through anaplerosis, OAA-pyruvate recycling and net gluconeogenesis, and given certain assumptions, simple mathematical equations relate the relative fractions of C2-isotopomers to the relative fluxes through these pathways.

The metabolic pathways of FIG. 1 were modeled using input-output methods as described elsewhere (Malloy et al., 1988) with the following assumptions: 1) metabolic and isotopic steady-state, 2) acetyl-CoA was derived from unenriched sources, 3) OAA was fully randomized in the symmetric 4 carbon pools, and 4) $^{13}CO_2$ did not contribute significantly to the bicarbonate pool involved in pyruvate carboxylation. Each flux variable was defined relative to flux through citrate synthase: $y_{pc}$, denotes flux through pyruvate carboxylation; $y_s$, flux into succinyl-CoA via propionyl-CoA carboxylase or an equivalent pathway; y, total anaplerosis= $y_{pc}+y_s$; PK, flux from phosphoenolpyruvate to pyruvate; and g, glucose production=(y−PK)/2 (division by 2 is necessary to convert the rate of PEP production to the rate of glucose production).

This analysis, like other isotopic studies of pyruvate recycling and gluconeogenesis, does not distinguish flux through the malic enzyme (ME) from the combined action of phosphoenolpyruvate carboxykinase (PEPCK) and pyruvate kinase (PK). Therefore in the equations presented below, PK+ME indicates the combined flux through the malic enzyme and pyruvate kinase. Although a complete $^{13}C$ isotopomer analysis of all gluconate (glucose) and glutamate multiplet areas provides a complete description of the metabolic pathways of FIG. 1, the constraints imposed by the assumptions stated above resulted in a few simple relationships:

| resonance studied | shift (ppm) | metabolic flux as calculated from areas under $^{13}C$ NMR peaks | reference |
|---|---|---|---|
| (1) glutamate C2 | 55.2 | y = (C2D23 − C2D12)/C2D12 | Katz et al., 1993 |
| (2) glutamate C2 | 55.2 | PK + ME = (C2D23 − C2Q)/C2D12 | Katz, 1985 |
| (3) glutamate C2 | 55.2 | g = (C2Q − C2D12)/(2 × 2D12) | Tayek and Katz, 1996 |
| (4) glutamate C3 | 27.8 | g = (C3D − 05)/(2—2 × C3D) | Cohen, 1981 |
| (5) gluconate C1 | 180 | g = (C1D − 0.5)/(2—2 × C1D) | Cohen, 1987 |
| (6) gluconate C2 | 75.9 | y = (C2D12 − C2D23)/C2D23 | Cohen, et al. 1981 |
| (7) gluconate C2 | 75.9 | PK + ME = (C2D12 − C2Q)/C2D23 | Strisower et al., 1952 |
| (8) gluconate C2 | 75.9 | g = (C2Q − C2D23)/(2 × C2D23) | Landau et al., 1993 |

These equations show that the $^{13}C$ NMR spectrum of either glutamate C2 or gluconate C2 yield a direct measure of anaplerosis (y), glucose production (g) and pyruvate kinase (actually PK+ME) flux while glutamate C3 and gluconate C1 provide a direct measure of g. Note that in the absence of pyruvate recycling (PK+ME=0), C2D23 would equal C2Q in glutamate, C2D12 would equal C2Q in gluconate, and the equations simplify to y=2 g.

The disclosed $^{13}C$ isotopomer method is easily adapted to human studies since it uses a nonradioactive tracer that can be given orally. Complex $^{13}C$-isotopomer distributions of glucose (obtained from blood samples) and phenylacetylglutamine and glucuronate (obtained from urine samples) produced by hepatic metabolism of [U-$^{13}C$]propionate can be analyzed in a straightforward manner using the method of the invention to measure gluconeogenesis and pyruvate recycling. A simple urine purification procedure retains both phenylacetylglutamine and glucuronide, thereby allowing a $^{13}C$-isotopomer analysis of both metabolites from a single $^{13}C$ NMR spectrum. The analyte pools, particularly the urinary products, provide sufficient material to quantitate isotopomer distributions by $^{13}C$-NMR at $^{13}C$ enrichment levels only 1–2% above natural abundance. $^{13}C$ NMR proved to be particularly valuable tool for direct isotopomer analysis of the glucuronide hexose skeleton, following its enzymatic hydrolysis from the parent acetaminophen β-glucuronide.

There are three advantages to the disclosed method compared to previously published methods. First, the determination of positional $^{13}C$ glucose isotopomers appears to be much simpler by $^{13}C$ NMR than by GC/MS (Beylot et. al., 1993). Second, others have isolated acetaminophen-β-glucuronide from urine and converted the glycone moiety to glucose by chemical reduction of the glycone C6 carboxyl followed by enzymatic cleavage of the β-glucoside product (Magnusson et. al, 1988, Ekberg et. al., 1995). Again, the chemical approach reported here appears simpler and provides complete recovery of labeled urinary glycones, an important consideration given the relatively low sensitivity of $^{13}C$ NMR compared to mass spectrometry methods. Finally, in situ hydrolysis of the β-glucuronide may have advantages in the clinical setting. A wide range of medications and drugs are cleared by glucuronidation, hence a patient has the potential to produce a complex cocktail of urinary β-glucuronides even in the absence of acetaminophen. For such an individual, collective hydrolysis in situ should be far easier than quantitative isolation, reduction and hydrolysis of the complex glucuronide mixture.

The method of the present invention is superior to previous methods of measuring gluconeogenic flux using singly-labeled substrates in that it is insensitive to reincorporation of the label into glucose and glutamate via carboxylation of labeled bicarbonate. Measurements of gluconeogenesis using singly-labeled substrates such as [3-$^{14}C$] lactate rely on determining the ratio of label in glucose C1/C3 or glutamate C2/C 1. These measurements are exquisitely sensitive to the reincorporation of label into glucose C3 and glutamate C1 via carboxylation of labeled bicarbonate (Magnusson et. al., 1990; Landau et. al., 1993). To obtain the necessary correction factors, an additional labeling experiment using labeled bicarbonate must be performed.

By comparison, the glucose and phenylacetylglutamine multiplets observed in the $^{13}C$ NMR spectra of these metabolites have differing degrees of sensitivity to enrichment from $^{13}C$-bicarbonate. The glucose C1 (and C6) and phenylacetylglutamine C3 multiplets are completely insensitive to contributions from $^{13}C$-bicarbonate since they originate from carbons 2 and 3 of oxaloacetate (Jones et al., 1997). After subtraction of natural abundance contributions, these multiplets give an estimate of g that requires no correction for $^{13}C$-bicarbonate contributions. Estimates of g from the gluconate C6 multiplets (2.39±0.84) and the phenylacetylglutamine C3 multiplets (1.67±0.71) are in good agreement with estimates of g from the C2 multiplets (see Table 3). This suggests that the C2 isotopomer ratios of these metabolites were not significantly weighted by $^{13}C$-bicarbonate enrichment.

The different flux estimates reported by hexose and phenylacetylglutamine indicate that hepatic glucose-6-phosphate and glutamine are sampling oxaloacetate pools that are not isotopically equivalent. Phenylacetylglutamine appears to be sampling a citric acid cycle pool that has a higher level of oxaloacetate-pyruvate recycling than the one sampled by either glucose or glucuronide. Labeling contributions from peripheral tissues such as the heart and skeletal muscle are unlikely to skew the flux estimates in this direction, since these tissues possess only modest anaplerosis and no significant OAA-pyruvate recycling activities (Szczepaniak et. al., 1996; Sherry et. al., 1988; Malloy et. al., 1987; Jeffrey et al., 1996). Therefore, the oxaloacetate pool reported by phenylacetylglutamine is probably hepatic in origin, demonstrating some degree of metabolic zonation or compartmentation within the intact human liver, at least with respect to propionate.

It is well established that hepatic glucose synthesis is highest in the periportal region, while glutamine synthetase is highly localized in the distal perivenous region. The high pyruvate-OAA recycling flux reported by phenylacetylglutamine does match an important characteristic of perivenous metabolism: a higher ratio of pyruvate kinase to PEP-carboxykinase activity compared to that found in the periportal zone (Jones et. al., 1996; Jungermann et. al., 1985; Jungermann et. al., 1987; Jungermann et.al., 1989). This suggestion has to be tempered by the fact that the perivenous zone is also reported to have relatively high pyruvate dehydrogenase activity (Jungermann et.al., 1989), which would be expected to result in significant acetyl-CoA and phenylacetylglutamine C4 enrichment. Also, a significant fraction of glutamine carbon skeletons are thought to originate from outside the perivenous region, including periportal contributions (in the form of glutamate).

Why are these labeling differences revealed with propionate but not with lactate? A difference in the hepatic metabolism of propionate vs. lactate is that the former is quantitatively extracted from the circulation, whereas the latter is not (Remesy et. al., 1983). Since mitochondrial density is highest in the periportal region of the liver (Wimmer et. al., 1989), it is possible that a propionate tracer is preferentially consumed by the periportal cells compared to a lactate tracer. Therefore, downstream regions could receive little direct labeling from propionate, while receiving significant contributions from secondary labeled products of periportal propionate metabolism, including glucose. Reutilization of hepatic glucose by the perivenous region is consistent with the zonal model of regulated hepatic glucose output proposed by Jungermann and others where periportal glucose synthesis is appropriately attenuated by perivenal glucose reutilization (Jungermann et. al., 1982; Jungermann et. al., 1985; Jungermann et. al., 1987; Jungermann et. al., 1989). Utilization of secondary-labeled products by the perivenous region could generate quite a different oxaloacetate isotopomer distribution compared to that produced from periportal metabolism of [U-$^{13}$C]propionate if the two regions have different metabolic flux characteristics. In contrast a lactate tracer is metabolized more uniformly across the lobule, and therefore generates an averaged labeling distribution in glucose and glutamine. The fact that glucose and glutamate were labeled equivalently in perfused rat livers supplied with supraphysiological and saturating levels of [U-$^{13}$C]propionate, lactate and pyruvate (Jones et al., 1997), suggests that intralobular substrate gradients may be an important determinant of labeling heterogeneity between different metabolites in the liver.

Since $^{13}$C is a non-radioactive isotope and bulk substitution of $^{12}$C by $^{13}$C is not known to have a significant kinetic isotope effect, substantial quantities of $^{13}$C-enriched substrates can be safely given to humans (Cline et. al., 1994; Gruetter et. al., 1992; Rothman et. al., 1992; Gruetter et. al., 1992). However, such experiments can generate supraphysiological substrate levels that could alter basal metabolic activities. In our study, fasted individuals ingested an average of 1.5 g propionate over one hour. Assuming quantitative capture of propionate by portal circulation and a portal vein blood flow of ~700 ml/min (Doi et. al., 1988), one can estimate that the average portal propionate concentration is no higher than 0.36 mM over the 1-hour period. Portal vein propionate concentrations averaging 0.03 mM have been reported in patients undergoing gall-bladder surgery, (Dankert et. al., 1981), but these probably represent fasting levels, which are likely to be much less than postprandial concentrations. The only other measurement of human portal vein propionate concentrations were obtained by autopsy of sudden death victims, where levels ranging from 0.02–0.19 mM were reported (Cummings et. al., 1987). Measurements of portal vein propionate levels in the pig, a good model for human digestion, indicated levels of 0.08 mM under fasting conditions and 0.25–0.40 mM following feeding (Topping et. al., 1985). These postprandial levels span the estimated portal vein propionate levels generated during the experimental protocol. Nonetheless, the fact that urinary [U-$^{13}$C]3-hydroxypropionate was detected in several subjects suggests that the hepatic propionyl-CoA carboxylase can become saturated (Ando et. al., 1972) and physiological consequences of saturating propionyl-CoA carboxylase in normal fasted humans is not known.

In rat hepatocytes, high levels of propionate can inhibit the activities of several enzymes by lowering the free CoA levels (Blair et. al., 1973; Patel et. al., 1983; Blass et. al., 1992), including pyruvate carboxylase. Since pyruvate carboxylase is the predominant anaplerotic pathway in the liver, inhibition of this enzyme can result in decreased gluconeogenic flux (Blair et. al., 1973; Chan et. al., 1972). However, in fasted humans, the provision of 1.2 grams of propionate over 3 hours did not alter hepatic glucose production in fasted volunteers (Laurent et. al., 1995) suggesting that hepatic gluconeogenesis was maintained under these conditions. Our study featured comparable amounts of ingested propionate (~1.5 grams), but the shorter ingestion period of our protocol probably generated higher levels of propionate in portal circulation. Nonetheless, our estimated portal vein propionate levels of 0.36 mM are still far below the 5–10 mM concentrations reported to inhibit gluconeogenesis and citric acid cycle fluxes (Blair et. al., 1973; Chan et. al., 1972, Matsuishi et. al., 1991).

NMR SPECTROSCOPY

Proton decoupled $^{13}$C NMR spectra of blood extracts were obtained using a 5 mm probe on a 9.4 T General Electric Omega spectrometer operating at 100.61 MHz. Free-induction decays were digitized into 32 K points and were routinely multiplied by a 0.5–1.0 Hz exponential prior to Fourier transform. Proton decoupled $^{13}$C NMR spectra of urine extracts were obtained with an Unity Anova 14.5 T spectrometer operating at 150.9 MHz. Free-induction decays were digitized into 44 K points and were multiplied by a 0.5 Hz exponential prior to Fourier transform. Spectra from both systems were analyzed by the NUTS curve-fitting program (Acorn NMR Inc., Fremont Calif.).

Individual multiplet areas are defined as a fraction of the total resonance area as described elsewhere (Jones et al. 1994; Malloy et al., 1990). $^1$H NMR spectra from the glutamate samples were obtained with and without $^{13}$C single frequency decoupling of the C2 resonance at 55.2 ppm. $^{13}$C-Enrichments of carbons in the glutamine moiety of phenylacetylglutamine were quantitated directly from the 13C NMR spectrum of the isolated phenylacetylglutamine using the method of Dugelay et al. (22). Gluconate $^{13}$C-enrichments were quantitated directly from the $^{13}$C NMR spectrum by comparing the total area of each gluconate resonance with the C2 resonance of the glycolate standard.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1
Liver Perfusion

Male Sprague-Dawley rats (175–275 g, Sasco, Houston, Tex.) were fasted overnight before their livers were isolated and perfused via cannulation of the vena porta as described previously (Seglen, 1976). The livers were flushed in situ for 10 min using non-recirculating Krebs-Henseleit bicarbonate buffer, pH 7.4, at 37° C. containing 2 mM NH$_4$Cl, 15 mM lactate, 1.5 mM pyruvate, 1.5 mM acetate, and 2 mM propionate at a flow rate of 50 ml/min. Oxygenation of the perfusion fluid was maintained by flow over an oxygenating net in a humidified atmosphere of air/CO$_2$ (95/5, v/v). The perfusion fluid was then switched to a fresh 300 ml portion of the modified Krebs-Henseleit buffer prepared with 2 mM sodium [1,2,3-$^{13}$C]propionate and recirculating perfusion was continued for 60 minutes to achieve steady-state conditions.

The tissue was then freeze-clamped, extracted, and freeze-dried. Glutamate was isolated by ion-exchange chromatography as described (Katz et al.,1993), freeze-dried and redissolved in D$_2$O for NMR analyses. The glucose content in deproteinized perfusion fluid samples and perchloric acid extracts of the freeze-clamped livers was determined using the hexokinase/glucose-6-phosphate dehydrogenase coupled assay (Bergmeyer et al., 1974). Glucose was quantitatively oxidized to gluconate by dissolving the lyophilized perfusion fluid sample in 10 rnl of 1 mM sodium phosphate buffer, pH 5.5 containing 100 units of glucose oxidase (Type VII-S, Sigma) and incubating the mixture for 3–12 hours at 25° C. with gentle bubbling (about 10–20 ml/min) of air (Jones et al., 1994). The reaction was terminated by adding 5 ml of 8% perchloric acid. Sodium [1,2,3-$^{13}$C$_3$]propionate and sodium $^{13}$C-bicarbonate (99% enriched) were obtained from Cambridge Isotope Labs (Cambridge, Mass.). Other materials were obtained from Sigma (St. Louis, Mo.).

Example 2
In vivo Rat Studies on Perfused Liver

Male Sprague Dawley rats weighing 280–350 g were anaesthetized (ketamine/xylazine) and intubated after an overnight fast. An esophagal tube was inserted for gastric feeding, and a catheter inserted into the jugular vein An aqueous solution of a [1,2,3-$^{13}$C]propionate was administered either into the stomach (at 5 min intervals for 15 min) or via the jugular vein (4 ml/hr for 30 min) at 400 mg propionate/kg body weight. When propionate was provided orally, saline was infused I.V., and vice versa. After 30 min, the liver was freeze-clamped and a sample of blood taken. These were extracted with perchloric acid, adjusted to pH 7.4 with KOH, freeze-dried, and dissolved in 600 µl of D$_2$O for analysis by $^{13}$C NMR.

Discussions. $^{13}$C enrichment in carbons 1, 2 and 3 of glutamate and gluconate were easily detected in extracts of isolated livers. The C2 resonances shown in FIG. 2 display extensive $^{13}$C-$^{13}$C coupling indicative of multiply-enriched isotopomers. The fractional enrichment in glutamate C2 was 0.174±0.047 (measured $^1$H NMR) while $^{13}$C enrichment of glutamate C4 was less than 2%, verifying the model assumption that labeling of acetyl-CoA was insignificant. The relative multiplets areas of glutamate C2 and gluconate C2 were identical (Table 1: note the inverse relationship between C2D12 and C2D23 of glutamate and gluconate). This indicates that 1) glutamate and glucose were derived from the same pool of OAA, and 2) OAA was fully randomized by exchange with symmetric TCA cycle intermediates.

Analysis of these data using equations 1–3 and 6–8 indicated that total anaplerotic flux, y, was about 4 times citrate synthase flux (see Table 1) while glucose production was about 1.2 times citrate synthase flux. There was no significant difference between the metabolic results derived from either spectrum. It is important to note that the equations for glutamate C2 and gluconate C2 do not contain a contribution from C2S and hence are insensitive to any natural abundance contributions to the spectra. The equations for glutamate C3 and gluconate C1 (eqns. 4 and 5) however would be sensitive to natural abundance contributions. After correcting for a small (~5%) natural abundance contribution to gluconate C1 and glutamate C3 as determined by $^1$H NMR, values of g estimated using equations 4 and 5 were not significantly different from the values estimated from the C2 multiplet areas (Table 1).

Glucose production in these isolated livers was 0.37±0.15 µmol/gww/min, compared a value of about 1 µmol/gww/min in the absence of propionate (Sherry et al., 1994). Blair et al. (1973) also reported a significant drop in glucose production by perfused rat livers to 0.42±0.06 µmol/gww/min when propionate (10 mM) was added to a mixture of L-lactate (10 rmM), and pyruvate (1 mM). Since the rate of gluconeogenesis relative to citrate synthase was about 1.15 (g in Table 1), then flux through citrate synthase in these livers can be estimated at 0.37/1.15=0.32 µmol/gww/min. This is comparable to values of 0.13 to 0.25 µmol/gww/min for citrate synthase reported by DiDonato and colleagues (DiDonato et al., 1993). This of course assumes that no glucose was derived from liver glycogen in these starved animals.

Table 1 shows gluconeogenesis and pyruvate recycling fluxes calculated from spin coupled multiplets in the $^{13}$C NMR spectrum of glutamate or gluconate from isolated rat livers. When [$^{13}$C]bicarbonate was available, gluconeogenesis (or glucose production) was calculated from the multiplets in carbon 1 or carbon 3 of gluconate or glutamate, respectively.

TABLE 1

| multiplets | glutamate | gluconate |
|---|---|---|
| C2S | 0.10 ± 0.02 | 0.10 ± 0.02 |
| C2D23 | 0.48 ± 0.01 | 0.10 ± 0.01 |
| C2D12 | 0.10 ± 0.01 | 0.48 ± 0.01 |
| C2Q | 0.32 ± 0.03 | 0.33 ± 0.01 |
| relative fluxes (without $^{13}$CO$_2$): | | |
| y, total anaplerosis | 3.91 ± 0.61 | 4.13 ± 0.32 |
| PK ± ME | 1.63 ± 0.51 | 1.65 ± 0.20 |

TABLE 1-continued

| multiplets | glutamate | gluconate |
|---|---|---|
| g, gluconeogenesis | 1.15 ± 0.19 | 1.24 ± 0.09 |
| (PK + ME)/y, pyruvate recycling relative fluxes (with $^{13}CO_2$): | 42% ± 8% | 40% ± 2% |
| g, gluconeogenesis | 1.14 ± 0.42 | 1.21 ± .17 |

All results are n = 4 or 5, mean ± s.d

The results reported in Table 1 are consistent with some but not all earlier reports. For example, Cohen, et al. reported that PK flux relative to gluconeogenesis was 0.74 to 1.0 in isolated livers (Cohen, 1987), while Grunnet and Katz (Grunnet and Katz, 1978) reported a range of PK/g from 0.18 to 0.72, and Friedman et al. found 0.86 in isolated livers (Friedman, et al., 1971). In comparison, the inventors' value of (PK±ME)/g was 1.3. Recent measurements reported (PK±ME),/$y_{PC}$ of 0.26–0.40 in normal rats (Petersen et al., 1994), in reasonable agreement with the inventors' finding of (PK+ME)/y=0.49 (where y=$y_s$+$y_{PC}$). On the other hand, results in Table 1 are in the low end of the range reported in humans by Magnusson et al. (1990) who found the following fluxes relative to citrate synthase: PK, 1.5 to 3.7; gluconeogenesis to 1.4 to 3.5; and total anaplerosis 2.8 to 7. This wide range of reported values for variables related to gluconeogenesis is likely due to variations in nutritional state, available substrates, and species differences. In some instances "gluconeogenesis" may indicate flux from phosphoenolpyruvate to glucose or the rate of glucose production.

Previous observations were made under conditions where the gluconate C2D12 was significantly larger than the gluconate C2Q in livers supplied with [1,2,3-$^{13}$C]propionate. This observation, confirmed here, was interpreted as evidence for incomplete randomization of symmetric 4 carbon citric cycle intermediates (Sherry, et al., 1994). It was pointed out that this multiplet pattern could also be observed whenever pyruvate recycling was significant (Sherry and Malloy, 1996). In these earlier reports the conclusions were solely based on the enrichment patterns detected in gluconate C2, aspartate C2 or lactate C2 (each reflecting the C2 carbon of OAA) and this did not provide sufficient information to distinguish between pyruvate recycling or orientation conserved transfer.

Glutamate was also examined because it was present in sufficient concentration for analysis, and comparison with gluconate allows the inventors to distinguish between these two metabolic possibilities. If orientation conserved transfer is the mechanism for gluconate C2D12>C2Q, then the glutamate C2Q should have been significantly larger than either doublet. This was not observed.

The alternative hypothesis, that gluconate C2D12>C2Q because of recycling, then glutamate C2D23>C2Q, exactly as observed. The inventors conclude that under these conditions the $^{13}$C spectra of glutamate and gluconate are consistent with significant pyruvate recycling but not consistent with orientation conserved transfer of symmetric intermediates. Furthermore, the inventors' observation that glutamate C2D23=gluconate C2D12 and glutamate C2D12= gluconate C2D23 shows that there was complete randomization of symmetric citric acid cycle intermediates and that both metabolites originated from a common OAA. This conclusion is consistent with most metabolic models of the liver, but it should noted that labeling studies with [1,2,3-$^{13}C_3$]lactate have shown significant differences in the labeling patterns of these metabolites (Katz et al., 1993; Des Rosiers et al., 1995). The inventors' finding that OAA was fully randomized is also consistent the conclusion by Landau and colleagues (Magnusson, et al., 1990) that backwards scrambling of OAA into the symmetric 4-carbon pool is rapid relative to citric acid cycle flux in humans.

Effect of $^{13}CO_2$ enrichment. The input-output analysis did not yield simple equations for carbon 2 of glutamate or glucose when $^{13}CO_2$ entered at the level of pyruvate carboxylase. Thus, equations 1–3 and 6–8 do not apply if $CO_2$ is significantly enriched. However, the glucose C1 multiplets and the glutamate C3 multiplets are not sensitive to $^{13}CO_2$ enrichment because $^{13}C$ entering the oxaloacetate pool via $CO_2$ can only enrich carbons 1 or 4 of OAA. Therefore, equations 4 and 5 are valid regardless of whether $^{13}CO_2$ contains enriched carbon or not. FIG. 2 compares representative glutamate and gluconate C2 multiplets derived from livers perfused with [1,2,3-$^{13}$C] propionate±$^{13}CO_2$. Note that the C2 multiplets were quite sensitive to the presence of $^{13}CO_2$ (C2Q now dominates both C2 resonances) while the multiplets in glutamate C3 and gluconate C1 did not change. Glucose production in livers perfused with $^{13}CO_2$ was 1.14±0.42 as reported by the glutamate C3 multiplet areas (equation 4) and 1.21±0.17 as reported by the gluconate C1 multiplet areas (equation 5), identical to the values determined in the absence of $CO_2$ enrichment (Table 1).

The abbreviations C1, C2, C3, C4 and C5 refer to the respective carbons of glutamate. In a pool of glutamate molecules consisting of a mixture of $^{13}C$ isotopomers, each glutamate resonance consists of from 1 to 9 lines, depending upon the position of the carbon within glutamate molecule and the labeling of the adjacent carbons. For example, the 5-line multiplet usually observed for glutamate C3 at 27.5 ppm is actually the sum of a single (carbons adjacent to the enriched C3 are unenriched), two equivalent doublets (C3 and either C2 or C4 are enriched), and a triplet (C2, C3 and C4 are all enriched). The doublets are equivalent because the coupling constant is nearly equal for C2–C3 and C3–C4. The relative areas of the individual components of the multiplet may be measured and, in this example (FIG. 2(b)), it may easily be determined that the singlet contributes 12%, the doublets 46%, and the triplet 42% to the total measured area of the multiplet. We designate these experimental measurements as C3S+C3D+C3T, respectively. Since C3S+ C3D+C3T=1, any two measurements determine the third. The C2 and C4 resonance multiplets may be similarly resolved into their individual components. The C2 and C4 components differ in one respect from C3 in that the coupling constants between adjacent enriched carbons are not equal. Hence, the C2 resonance, for example, may contain two doublets, and these are designated C2D12 and C2D23 to indicate which of the carbons adjacent to C2 is also enriched.

$F_c$ refers to the fractional enrichment in $^{13}C$ of the acetyl-CoA pool which condenses with OAA to form citrate. $F_{c0}$ indicates the fraction of the acetyl-CoA that is unlabeled. $F_{c1}$, $F_{c2}$, and $F_{c3}$ refer to the fraction of acetyl-CoA that is labeled in C1, C2 or C1 and C2, respectively. By definition, $F_{c0}$+$F_{c1}$+$F_{c2}$+$F_{c3}$=1. The second variable, y relates to the total flux through the anaplerotic reactions (a) to the total flux through citrate synthase (c), or y=a/c. Since the concentration of the citric acid intermediates are not changing in steady state, it was assumed that the pathways for removal of carbon skeletons are as active as those for entrance of carbon skeletons. The third group of variables refers to the $^{13}C$ labeling of carbon skeletons entering the citric acid cycle via the various anaplerotic pathways. $F_{a0}$ indicates the fraction of anaplerotic substrate that is unlabeled and $F_{a1}$ is the fraction of substrate that will yield either [2-$^{13}$C] oxaloacetate or [3-$^{13}$C] oxaloacetate in the first span of the citric acid cycle. By definition, $F_{a0}+F_{a1}=1$. Although the equations presented in the Appendix are perfectly general and include each of these variables, it is possible to choose labeled substrates which permit a considerable simplification of these equations. For example, [3-$^{13}$C] pyruvate and [2-$^{13}$C] acetate can only produce [2-$^{13}$C] acetyl CoA; hence, $F_{c1}$ and $F_{c3}$ are zero and $F_{c0}+F_{c2}=1$. Furthermore, we have chosen to limit our analysis to the protonated carbon resonance of glutamate (C2, C3 and C4) to avoid $T_1$; and nuclear Overhauser enhancement differences which may distort the individual multiplet components of the nonprotonated C1 and C5 resonance. Within these constraints, the equations simplify to:

$$C2S+[2(y+1)^2-2F_{c2}(y+1)-F_{c2}+(F_{c2})^2/(2(y30\ 1)^2)$$

$$C2D12=F_{c0}+F_{c2}/(2(y+1)^2)$$

$$C2D23=F_{c2}(2+2y-F_{c2})/(2(y+1)^2)$$

$$C3S=F_{c0}(F_{c0}+y)/(y+1)$$

$$C3T=(F_{c2})^2/(y+1)$$

$$C4D34=(yF_{a1}+F_{c2})/(2y+1)$$

The relative areas of the multiplets were measured from the $^{13}$C NMR spectrum by peak integration using the NMC software, by triangulation (peak height×width at half-height) and by plotting and weighing each resonance. There were no differences among the methods. Three independent variables ($F_{c2}$, y and $F_{a1}$) were evaluated for each perfusion condition using ZZSXQ, a Levenberg-Marquardt algorithm from the International Mathematical and Statistical Library, Houston, Tex., run on a December 10 at The University of Texas Health Science Center, Dallas. The program permitted solutions with the following boundary conditions: $1>F_{c2}>0$, $F_{c0}+F_{c2}=1$, $y>0$, $1>F_{a1}>0$). The results for group 8 were obtained using the more general equations (since $F_{a3}>0$). It should be noted that substrate containing any level of $^{13}$C enrichment may be used in those experiments, but the final fractional enrichments ($F_a$ and $F_c$) must be corrected if the level of $^{13}$C enrichment is below 99%. All results are expressed as the mean+standard deviation.

| | Glossary |
|---|---|
| CiF | Fraction of carbon in position i that is $^{13}$C |
| C1S | Area of singlet/C-1 resonance area |
| C1D | Area of doublet/C-1 resonance area, where C1S + C1D = 1 |
| C2S | Area of singlet/C-2 resonance area |
| C2D12 | Area of doublet (C-1, C-2)/C-2 resonance area |
| C2D23 | Area of doublet (C-2, C-3)/C-2 resonance area |
| C2Q | Area of quartet/C-2 resonance area, where C2S + C2D12 + C2D23 + C2Q = 1 |
| C3S | Area of singlet/C-3 resonance area |
| C3D | Area of doublet/C-3 resonance area |
| C3T | Area of triplet/C-3 resonance area, where C3S + C3D + C3T = 1 |
| C4S | Area of singlet/C-4 resonance area |
| C4D34 | Area of doublet (C-3, C-4)/C-4 resonance area |
| C4D45 | Area of doublet (C-4, C-5)/C-4 resonance area |
| C4Q | Area of quartet/C-4 resonance area, where C4S + C4D34 + C4D45 + C4Q = 1 |
| C5S | Area of singlet/C-5 resonance area |
| C5D | Area of doublet/C-5 resonance area, where C5S + C5D = 1 |
| $F_{ai}$ | Fractional enrichment of a substrate for an anaplerotic reaction |

| | -continued |
|---|---|
| | Glossary |
| $F_{a0}$ | Fraction of an anaplerotic substrate that is not enriched |
| $F_{a1}$ | Fraction of an anaplerotic substrate that yields oxaloacetate enriched in C-2 or C-3, where $F_{a0} + F_{a1} = 1$ |
| $F_{ci}$ | Fractional enrichment of a substrate for citrate synthase, acetyl-CoA, which provides one pathway for carbon entry into tricarboxylic acid cycle |
| $F_{c0}$ | [[1,2-$^{12}$C] acetyl = CoA]/[acetyl-CoA] |
| $F_{c1}$ | [[1-$^{13}$C] acetyl = CoA]/[acetyl-CoA] |
| $F_{c2}$ | [[2-$^{13}$C] acetyl = CoA]/[acetyl-CoA] |
| $F_{c3}$ | [[1,2-$^{13}$C] acetyl = CoA]/[acetyl-CoA], where $F_{c0} + F_{c1} + F_{c2} + F_{c3} = 1$ |
| y | Ratio of flux through combined anaplerotic reactions (a) relative to citrate synthase (c) = a/c |

Example 3

In vivo Gluconeogenesis Measurements from Blood Samples

Figure 3:
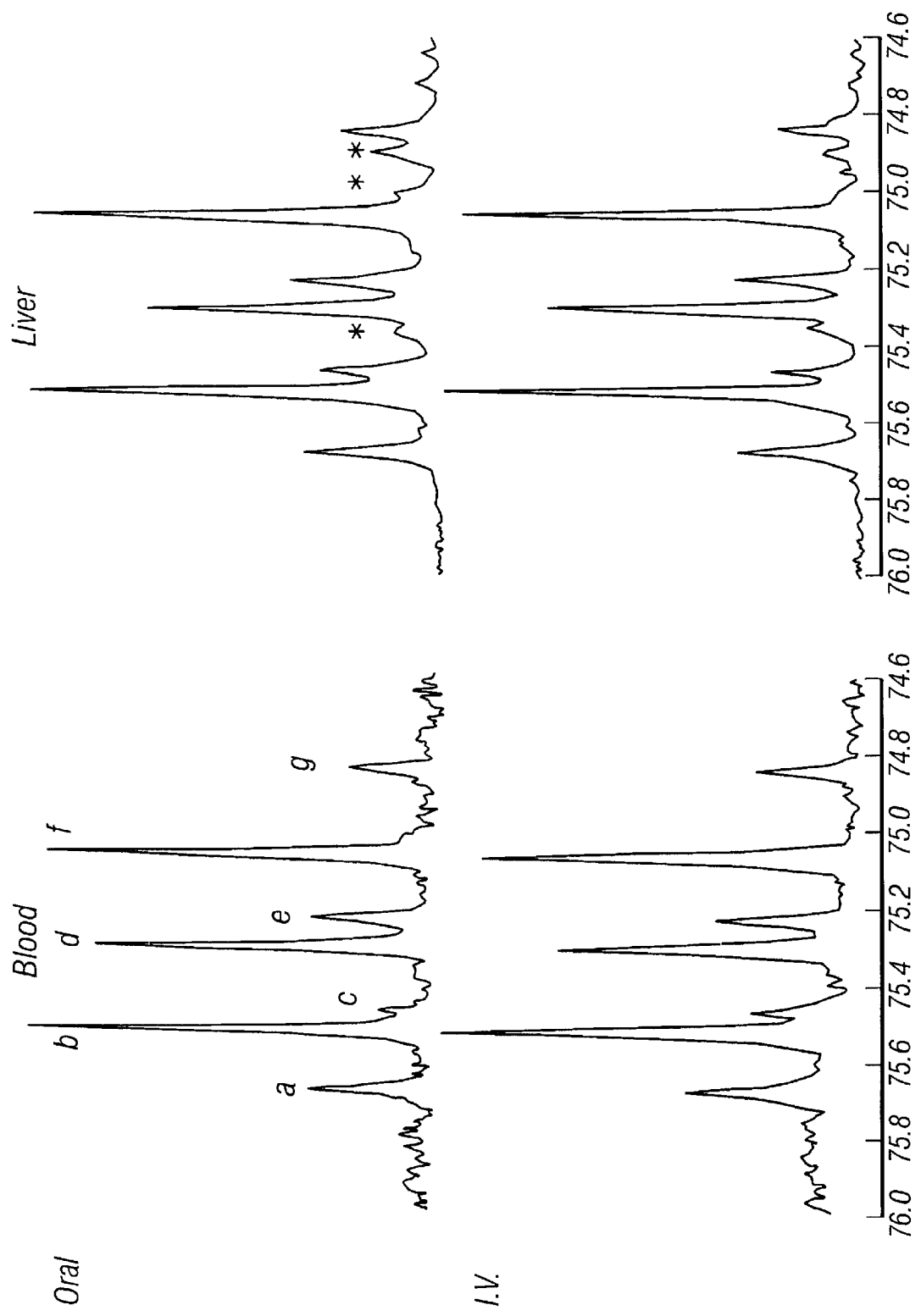
FIG. 3 shows the $^{13}$C NMR spectra of carbon 2 of the β anomer of glucose from blood or liver after intravenous or intragastric administration of [1,2,3-$^{13}$C]propionate. Each resonance in the C2 multiplet is labeled (a–g); further assignments are discussed in the text. The resonances labeled "*" are not assigned, but were observed only in the spectra obtained from liver extracts.

Although high quality spectra were obtained from the isolated perfused liver, the inventors also tested whether the disclosed analysis could be applied in vivo where numerous other substrates are also available for gluconeogenesis and whether the analysis could be done on blood glucose without prior oxidation to gluconate. $^{13}$C NMR spectra of glucose was obtained from both blood and freeze clamped liver after either oral (n=3) or intravenous (n=3) administration of [U-$^{13}$C]propionate. The β-C2 resonance of glucose was sufficiently resolved from all other resonances to allow an analysis of multiplet areas (FIG. 3). All four spectra confirm a high level of $^{13}$C enrichment with complex isotopomer mixtures, and there were no significant differences between the β-glucose C2 multiplets from blood versus liver tissue.

Three of the four quartet components of the C2 resonance were resolved (labeled a, e and g in FIG. 3). The fourth resonance overlapped with the central singlet d in FIG. 3. The relative intensities of each resonance in the quartet were calculated (Abraham et al., 1988) from the known coupling constants ($J_{12}$=47.0 Hz; $J_{23}$=38.5 Hz), field strength and chemical shifts of carbons 1, 2 and 3. Given the theoretically expected ratios of intensities, the contribution of the quartet to resonance d could be estimated by comparison with the measured areas of a, e and g. Using the same approach, resonance f was resolved into separate contributions from the C2D12 and the C2D23. The glucose C2D12 was 0.50±0.04, 0.49±0.02, 0.46±0.06, and 0.44±0.06 in the 4 groups (i.v. administration of propionate and blood sampled; i.v. propionate and liver sampled; oral propionate and blood sampled; oral propionate and liver sampled, respectively) which was not significantly different from the results obtained in the isolated liver (Table 1). The glucose C2D23 was 0.10±0.01, 0.09±0.01, 0.05±0.02. and 0.09±0.01 in the 4 groups, and the glucose C2Q was 0.29±0.03, 0.28±0.02, 0.25±0.05, and 0.28±0.03, respectively. These multiplet areas, when substituted into equations 6–8, gave the following results: y=4.57±1.15, PK±ME=2.26±0.75 (pyruvate recycling=49%), and g=1.16±0.25. Anaplerosis and PK±ME were slightly higher in vivo compared to the isolated liver (Table 1) gluconeogenesis was identical.

Efficacy of Method on Diseased Rats. Acute liver injury was induced in male Sprague-Dawley rats (190–310 g) to test the efficacy of the method as a diagnostic tool of liver disease. Injury was induced in a test group by orally administering a 1:1 mixture of $CCL_4$ and corn oil (1 mL/240 g body weight), 24 hours prior to surgery. After treatment, the test group was divided into two samples, one of which was fasted while the other was fed ad libidum. A control sample was similarly divided and either fed or fasted 24 hours prior to surgery.

The test animals were infused with an aqueous solution of [U-$^{13}$C$_3$]proprionate (150 mg/kg body weight) and [1,6-$^{13}$C$_2$]glucose (28 mg/kg body weight) via a jugular vein at a constant rate for 1 hour. Subsequently, a sample of blood was removed, centrifuged to separate out red cells and treated with perchloric acid to remove all plasma proteins. Blood glucose was oxidized to gluconate prior to $^{13}$C NMR analysis. Total blood glucose was significantly lower in animals treated with CCL$_4$ Analysis of the $^{13}$C NMR spectra resulted in the metabolic data reported in table 2. As seen in the table, the relative gluconeogenic flux (g) was significantly higher in rats with chemical damage due to CCL$_4$ treatment. This demonstrates the ability of the invention to detect altered liver metabolism resulting from acute hepatic injury.

Table 2 shows metabolic fluxes as measured in both fasted and fed rats with both healthy and diseased livers according to the method of the invention. All fluxes are measured relative to the TCA cycle flux.

TABLE 2

| Group | Anaplerosis (y) | Pyruvate Recycling (PK + ME) | Gluconeo-genesis (g) | Glucose Turnover ($\mu$mol/kg/min) |
|---|---|---|---|---|
| Fed Control | 3.68 ± 0.42 | 2.87 ± 0.42 | 0.40 ± 0.05 | No Data |
| Fed CCL$_4$ Treated | 4.00 ± 0.59 | 2.65 ± 0.42 | 0.67 ± 0.12 | No Data |
| Fasted Control | 3.92 ± 0.37 | 2.55 ± 0.52 | 0.69 ± 0.08 | 58 ± 2 |
| Fasted CCL$_4$ Treated | 5.03 ± 0.48 | 3.22 ± 0.49 | 0.90 ± 0.11 | 43 ± 8 |

Example 4

Application of the Method Utilizing a [1,6-$^{13}$C$_2$]Glucose Tracer

The inventors' approach takes advantage of the fact that complex mixtures of glucose isotopomers are readily resolvable and quantifiable by $^{13}$C and $^1$H NMR, including the irreversible tracer, [1,6-$^{13}$C$_2$]glucose. When infused as a small fraction of the total body glucose, this substrate is metabolized to produce two singly-labeled triose phosphates, and because of the high dilution, the probability for resynthesis of [1,6-$^{13}$C$_2$]glucose is insignificant. Glucose turnover is simply the dilution of infused [1,6-$^{13}$C$_2$]glucose multiplied by the infusion rate.

Figure 4:
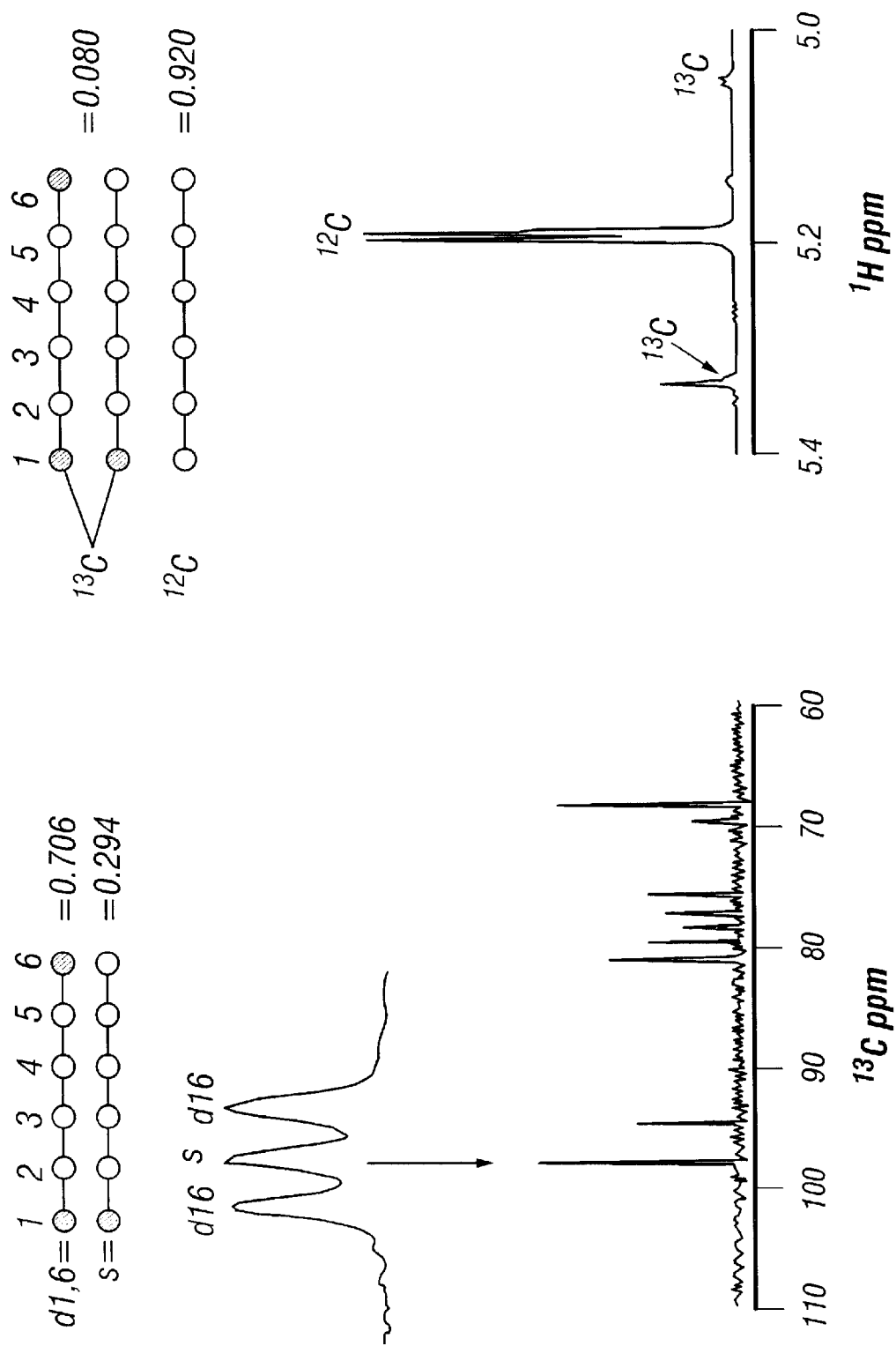
FIG. 4 shows glucose $^{13}$C and $^1$H spectra obtained after a primed infusion of [1,6-$^{13}$C]glucose at 0.49 mg/kg/min and unlabeled propionate at 2.48 mg/kg/min into the jugular vein of a fasted rat.

FIG. 4 shows glucose $^{13}$C and $^1$H spectra obtained after a primed infusion of [1,6-$^{13}$C$_2$]glucose (0.49 mg/Kg/mm) and unlabeled propionate (2.48 mg/Kg/min) into the jugular vein of a 24-hour fasted rat. The gluconate C2 carbon is adjacent to a carboxyl carbon and a secondary alcohol carbon, with different coupling constants to each ($J_{C1-C2}$=52 Hz and $J_{C2-C3}$=42 Hz as measured from the uniformly labeled gluconate C2 doublet of doublets). Hence, the gluconate C2 multiplet can have as many as nine lines: a singlet (C2 enriched only), two different doublets (C1 and C2 enriched or C2 and C3 enriched), and a doublet of doublets or a quartet (C1, C2, and C3 enriched). The resulting nine-line resonance is virtually identical to that observed for the glutamate C2 resonance in samples where glutamate C1, C2, and C3 can all become enriched in $^{13}$C. Since carbons 3, 4, and 5 of gluconate each have next nearest neighboring carbons that are chemically similar, these coupling constants are also quite similar (38 to 41 Hz) and, consequently, these resonances can have as many as five lines: a singlet, a doublet from $^{13}$C on either neighbor, and a pseudotriplet consisting of two superimposed doublets from $^{13}$C enrichment in both neighbors. The center component of this pseudotriplet usually overlaps any singlet component. These multiplets resemble the glutamate C3 multiplet following random $^{13}$C enrichment of glutamate C2, C3, and C4. Maximizing the chemical shift difference between the C3 and C5 resonances of gluconate now becomes important, since each five-line multiplet can potentially span over 80 Hz (the width of the triplet).

Figure 5:
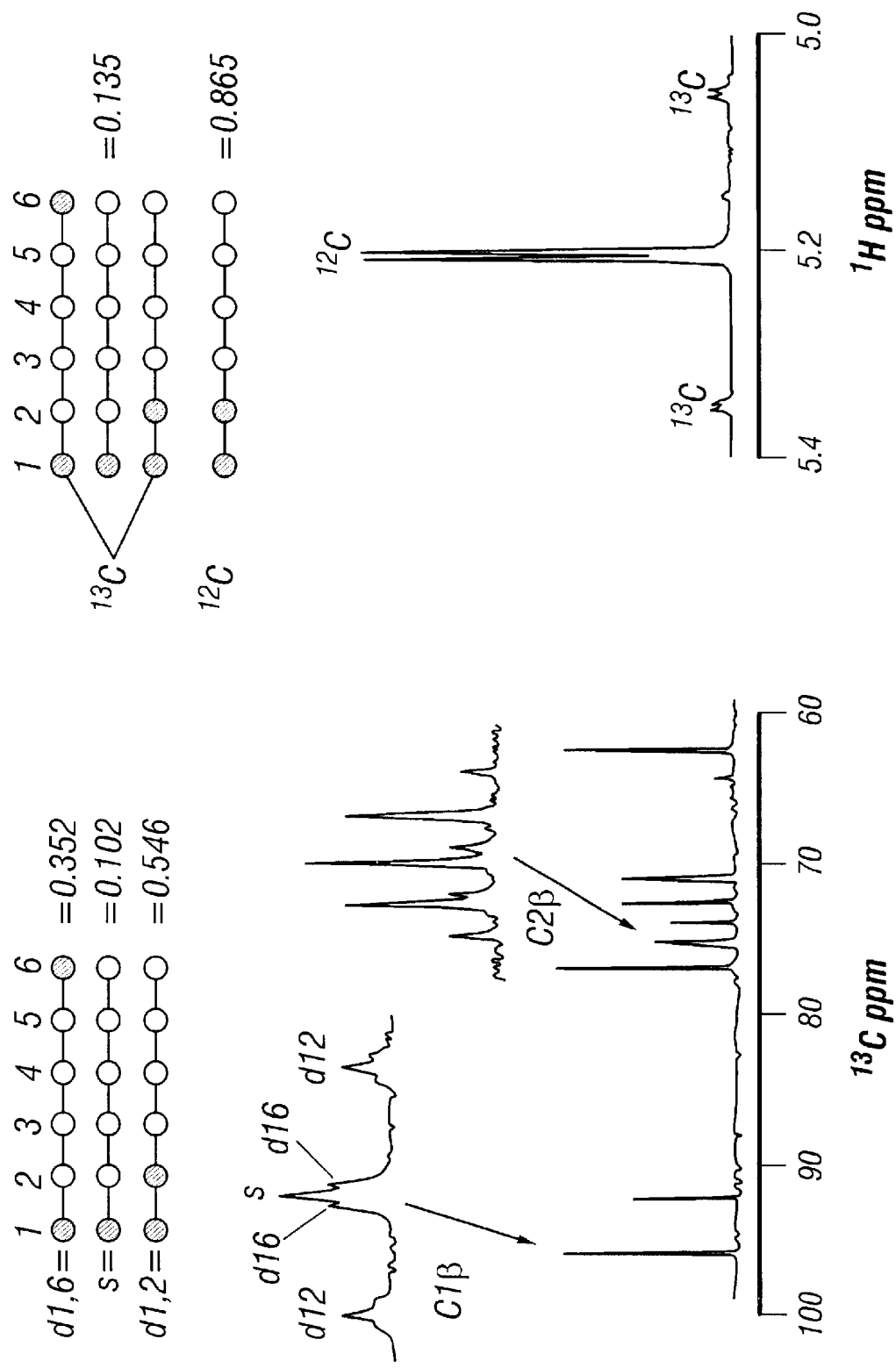
FIG. 5 shows the glucose C1 and C2 multiplet showing the simultaneous infusion of [U-$^{13}$C]propionate and [1,6-$^{13}C_2$]glucose.

The C3, C4, and C5 triplets show deviations from the standard binomial 1:2:1 distribution of intensities due to similar magnitudes for chemical shift differences and coupling constants for the C4/C3 and C4/C5 pairs at 9.4T (400 MHz $^1$H) (12). The nomenclature used in glutamate multiplet analysis was also used to assign the various multiplet components of gluconate; hence the singlet=S; doublet=D, pseudotriplet=T, and the quartet arising from a doublet of doublets=Q. The ability to distinguish and quantitate [1,6-$^{13}$C$_2$]-glucose by $^{13}$C NMR[10] allows the rate of glucose turnover to be easily measured. The values obtained for glucose turnover (10.37 mg/Kg/min) is consistent with published values of 8–10 mg/Kg/min. FIG. 5 shows the glucose C1 and C2 multiplet following simultaneous infusion of [U-$^{13}$C]propionate and [1,6-$^{13}$C$_2$]glucose. Despite the more complex and extensive labeling of plasma glucose, the [1,6-$^{13}$C$_2$]glucose signal is still quantifiable and allows glucose carbon turnover to be calculated from the C1 analysis.

There is no significant production of [1,6-$^{13}$C$_2$]glucose expected from hepatic metabolism of [U-$^{13}$C]propionate, hence the labeling from [U-$^{13}$C]propionate does not interfere with the glucose turnover measurement and the estimate (10.23 $\mu$mol/min/Kg) is consistent with the earlier one. Correspondingly, there is no significant production of multiply-labeled glucose C2 isotopomers from the [1,6-$^{13}$C$_2$]glucose label, hence it does not interfere with the quantitation of total anaplerotic flux from analysis of the C2$\beta$ multiplet ratios.

Isotopomer analysis indicates that total inflow into oxaloacetate was about 4 times the citric acid cycle flux, with about 50% of the carbons having been recycled between OAA and pyruvate leaving a net anaplerotic outflow of about 2 times the citric acid cycle flux, consistent with the inventors' recent published values. Carbons from [U-$^{13}$C] propionate contributed approximately 7% of the total anaplerotic outflow. Given the propionate infusion rate of 25 $\mu$mol/Kg/min, quantitative utilization of propionate by the liver would result in a net anaplerotic outflow of 357 $\mu$mol/Kg/min of triose equivalents, much higher than the 111 $\mu$mol/Kg/min accounted for by gluconeogenesis. However, this calculation does not take into account the effects of peripheral uptake and metabolism of [U-$^{13}$C]propionate This may decrease the amount of propionate incorporated into hepatic gluconeogenesis and inflate the estimate of absolute anaplerotic outflow.

Example 5

Figure 8:
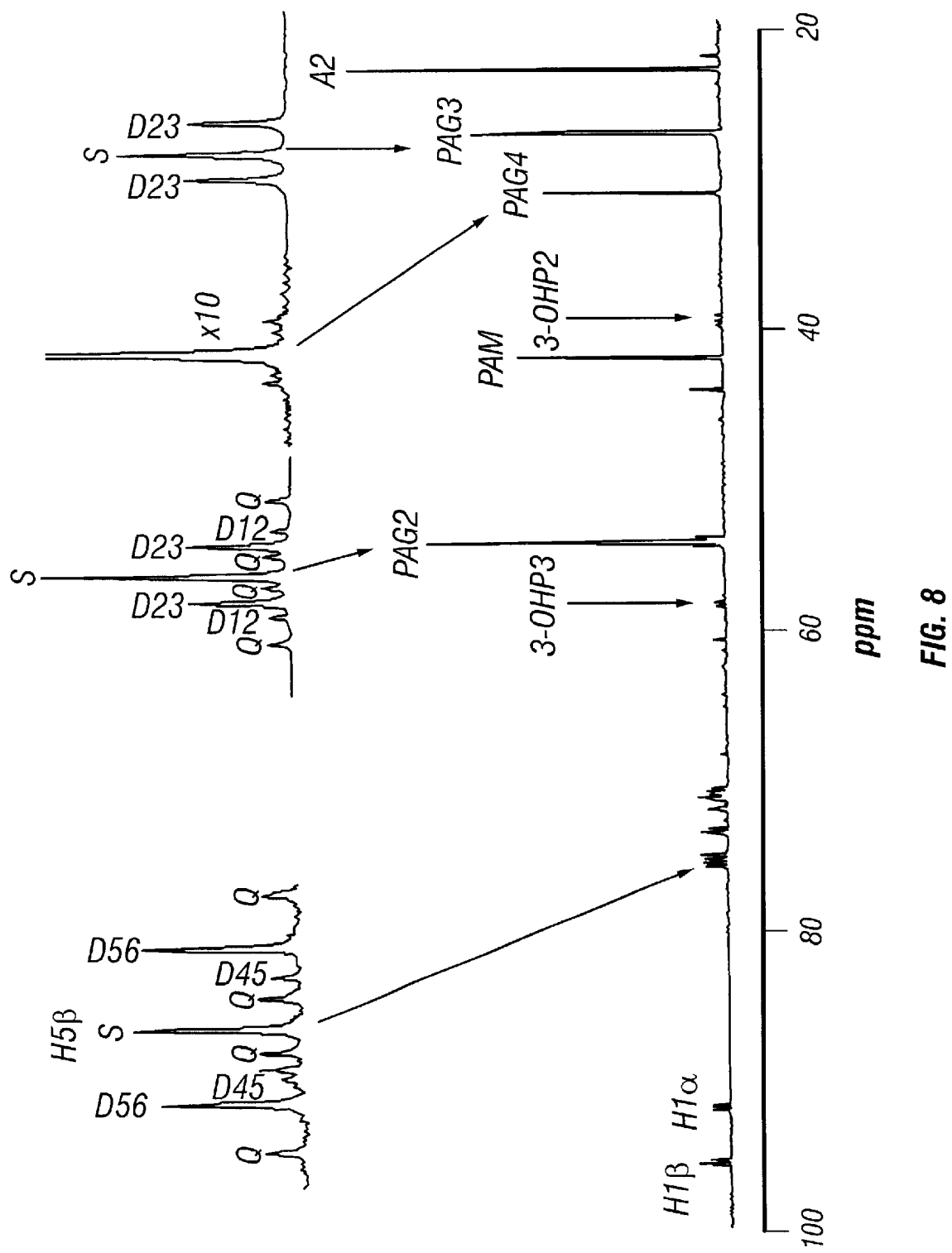
FIG. 8 shows the 20–100 ppm region of the $^{13}$C NMR spectrum of a purified urine extract obtained 2–3 hours after ingestion of [U-$^{13}$C]propionate. PAG2, PAG3 and PAG4 are carbons 2, 3 and 4 of the glutamine moiety of phenylacetylglutamine; PAM is the methylene carbon of the phenylacetyl moiety of phenylacetylglutamine;H1α, H1β and H5β are carbons 1α, 1β and 5β of glucuronate;3-OHP2 is carbon 2 of 3-hydroxypropionate; 3-OHP3 is carbon 3 of 3-hydroxypropionate;A2 is carbon 2 of acetate.

In Vivo Measurements in Human Subjects Based Upon $^{13}$C NMR Spectra of Blood Glucose and Urinary Glucuronide and Phenylacetylglutamine Six healthy subjects (5M, 1F), ages 23–33 years, and weighing between 60–88 Kg (76±12) were studied. Subjects were fasted for 24 hours prior to the start of the experiment and allowed access to water. FIG. 8 shows a flow-chart of drug ingestion and blood/urine sampling. From 7.00–8.00 a.m. the day of the study, each subject ingested 66mg/Kg phenylacetic acid distributed in 12 gelatin capsules (Gallipot Inc., St. Paul, Minn.). At 8.00 am, each subject ingested 2 tablets (500 mg each) of acetaminophen, and the first blood sample was also drawn into heparinized tubes (25 or 30 mls). Over the next hour, five of the subjects ingested a total of 20 or 25 mg/Kg sodium [U-$^{13}$C]propionate distributed in 6 gelatin capsules, while the sixth subject received 17 mg/Kg of the sodium [U-$^{13}$C]propionate. Following the 8.00 am sample, blood was drawn at 20 minute intervals over the next 2 hours with additional draws at 2.5 and 3 hours, (total blood drawn was 225 or 270 ml). Urine was also collected every hour over a 6 hour period starting at 9.00 am, with the exception of one individual, whose urine was collected every 2 hours.

Blood samples were chilled and centrifuged at 4° C. in heparinized tubes immediately after being drawn. The plasma was deproteinized by addition of 0.5 mls of ice-cold 70% perchloric acid, and the precipitated protein removed by centrifugation. The supernatant was adjusted to pH 5.0 with potassium hydroxide, and the insoluble potassium perchlorate was removed by a second centrifugation. The glucose content of each sample was assayed enzymatically before oxidation to gluconate with glucose oxidase. The samples were deproteinized a second time and the pH adjusted to 10.0 with KOH before lyophilization. Samples were resuspended in 600 µl D$_2$O containing a potassium glycolate standard where the glycolate carbons had natural abundance $^{13}$C (assumed to be 1.11%). For each NMR sample, the amount of glycolate added was equal to the amount of glucose assayed in the parent plasma extract (typically 20–40 micromoles).

A portion of each urine sample (50–100 ml) was adjusted to pH 7.0, incubated overnight with 10,000 U of urease to remove urea, then deproteinized with perchloric acid, neutralized with KOH then lyophilized and resuspended in D$_2$O to form a crude NMR sample. These samples frequently contained a mixture of the intact acetaminophen glucuronide and α,β-D-glucuronate formed from partial hydrolysis of the glucuronide. To convert the remaining glucuronide to glucuronate, the crude NMR sample was recombined with the unused urine portion, the pH was adjusted to 7.0 followed by incubation for 24 hours at 37° C. with 10,000 Fishman units of E. coli β-glucuronidase. A trace of sodium azide was also added to inhibit possible infection from airborne microorganisms.

The samples were deproteinized by perchloric acid and centrifuged, the supernatant pH was adjusted to 10.0 and the sample was left at room temperature for 30 minutes. (This last step hydrolyzed any glucuronolactone that might have formed from the nascent glucuronate during incubation). The pH was then adjusted to 8.0, the sample was loaded on to a 5–7 ml volume anion-exchange column (Dowex-1X8-acetate), and the column was washed with 40 ml of water. Phenylacetylglutamine and α,β-D-glucuronic acid were released by eluting with 15 mls of 10 M acetic acid. This fraction was lyophilized and resuspended in 700 µl D$_2$O. The pH was then adjusted to 9.0 with NaOD, the samples were centrifuged at 13,000 rpm with an Eppendorf centrifuge and the supernatants pipetted into 5 mm NMR tubes for NMR analysis.

Estimations of total anaplerotic inflow into oxaloacetate (y), recycling of OAA carbons via pyruvate (pk) and net gluconeogenic flux (g) (all relative to flux through citrate synthase) were calculated from the $^{13}$C-$^{13}$C spin-coupled multiplets of gluconate C2, phenylacetylglutamine C2, and β-D-glucuronate C5 using the methods described above.

Figure 6:
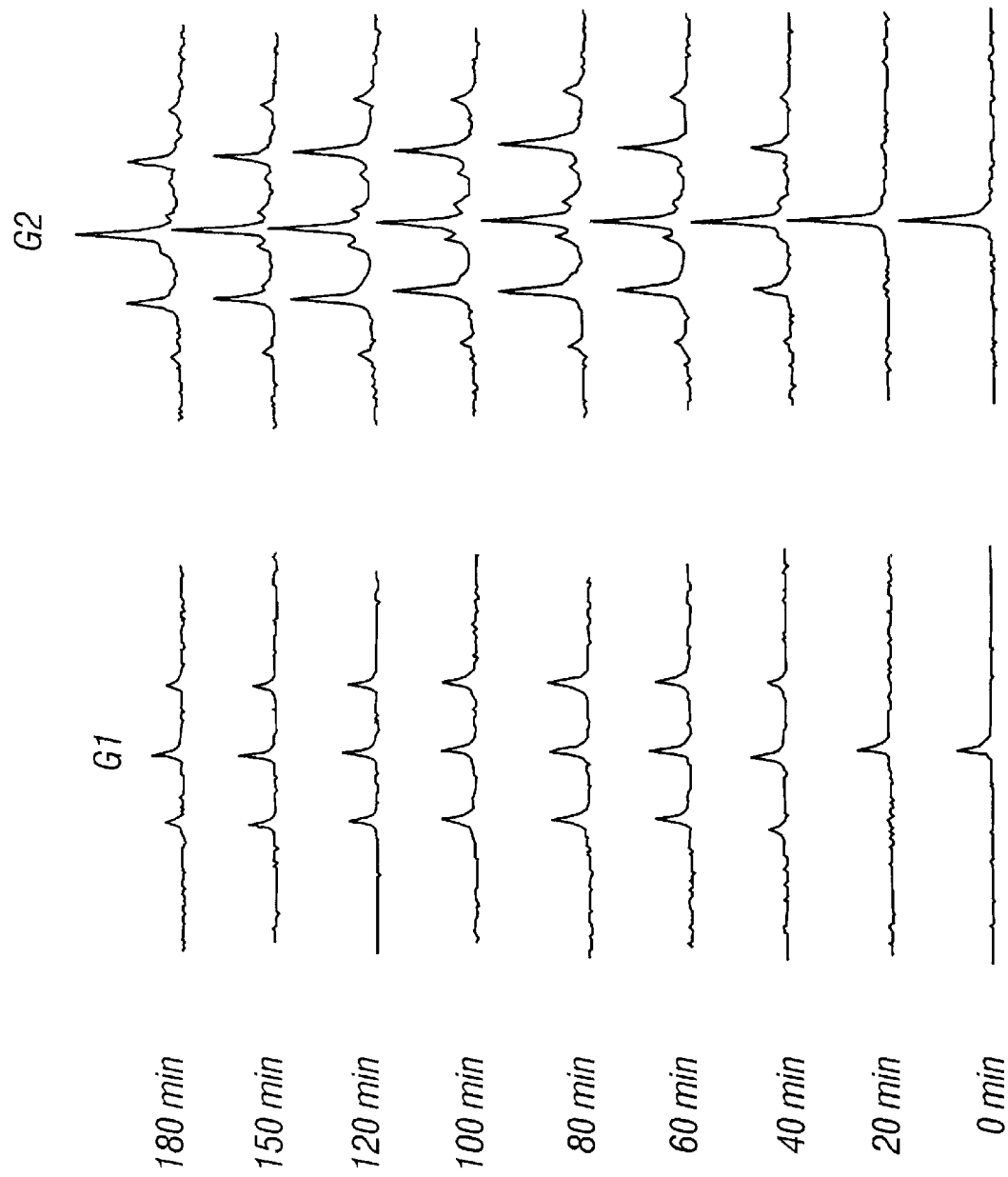
FIG. 6 shows the changes over time in the $^{13}$C NMR spectra of gluconate carbons 1 (GL1) and 2 (GL2) from a set of blood drawn from a single human subject over the indicated time periods following the ingestion of [U-$^{13}$C] propionate.
Figure 7:
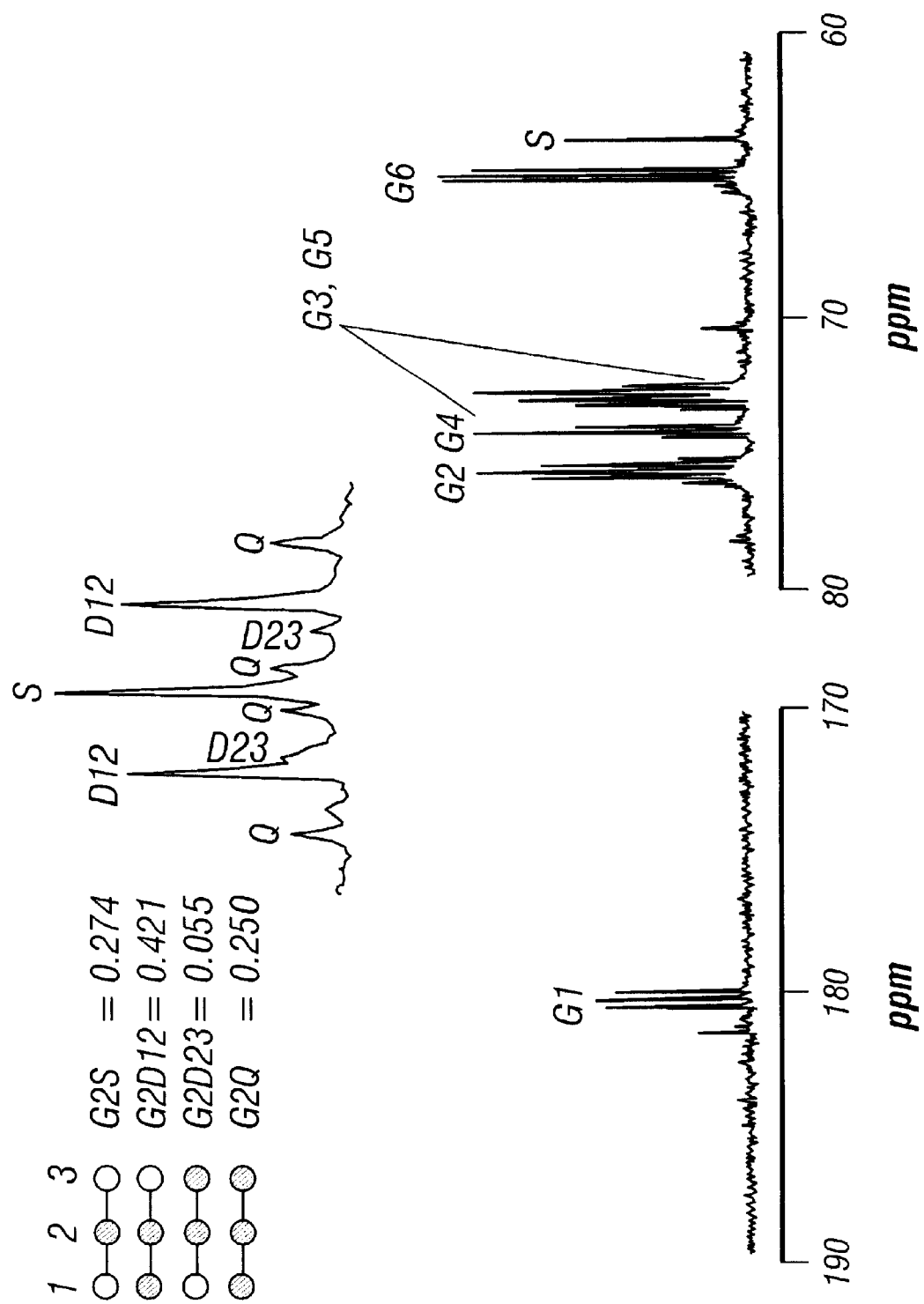
FIG. 7 shows the full $^{13}$C gluconate spectrum from the 120 min blood sample of the subject of FIG. 6 with an expanded view of the C2 resonance. In the inset, S refers to a singlet resonance of carbon 2; D12 to a doublet resonance arising from coupling between carbons 1 and 2; D23 to a doublet resonance arising from coupling between carbons 2 and 3; Q to a quartet arising from coupling of carbon 2 with carbons 1 and 3.

Discussion. FIG. 6 shows $^{13}$C NMR spectra of gluconate C1 and C2 from a set of blood draws of a single individual. Initially, only singlet resonances from natural abundance $^{13}$C were detected, but at 20 and 40 minutes, [U-$^{13}$C] propionate conversion into glucose already was evident from the appearance of $^3$C-$^{13}$C spin-coupled multiplets in the all six gluconate resonances. The intensity of the multiplet resonances increased steeply until 120 minutes, and between 120 and 180 minutes they remained relatively constant. In all subjects, the 9-line C2 gluconate multiplet was clearly formed at 120 minutes, and the ratios of multiplet components remained constant through 150 and 180 minutes. Carbons 1, 2, 5 and 6 of gluconate showed identical enrichment kinetics, reaching a peak enrichment of about 5% (Enrichment values include the natural abundance $^{13}$C contribution (assumed to be 1.11%)), while carbons 3 and 4 reached peak enrichments of about 3%. Between 120 and 180 minutes, enrichment of all six gluconate carbons remained relatively constant. FIG. 7 shows the full gluconate $^{13}$C NMR spectrum from the 120 minute blood sample with an expanded view of the C2 resonance. The 9-line C2 resonance can be resolved into contributions from all four possible labeling combinations of C2-enriched triose units. Their relative ratios provide an insight into the relative activities of the metabolic pathways involved in converting propionate and other anaplerotic substrates to glucose as previously described.

The time-course of urinary phenylacetylglutamine enrichment was similar to that of blood glucose, with peak enrichments being achieved 2–3 hours after ingestion of propionate. However, the $^{13}$C fractional enrichment in C1, C2, and C3 of phenylacetylglutamine was significantly lower than that of C1, C2, C5 or C6 of glucose or glucuronate. This difference is thought to be due to dilution of the glutamine pool by inflow of unenriched glutamine from peripheral tissues such as skeletal muscle (Magnusson et. al. 1990, Landau et. al. 1993). FIG. 8 shows the 20–100 ppm region of a $^{13}$C NMR spectrum of urine collected 2 hours after the last propionate ingestion. The C2, C3, and C4 resonances of the glutamine moiety of phenylacetylglutamine are prominent as is the natural abundance signal of the phenylacetyl methylene carbon at 43 ppm. The phenylacetylglutamine C2 and C3 resonances appear as multiplets arising from $^{13}$C-$^{13}$C spin-spin coupling, while the C4 resonance is largely a singlet (flanked by a weak doublet) arising primarily from natural abundance levels of $^{13}$C. This indicates that little of the $^{13}$C enriched gluconeogenic precursors that leave the cycle actually reenter the cycle pools via acetyl-CoA, thus validating one important simplification of the metabolic model (21).

Several key glucuronate multiplets are also fully resolved in the $^{13}$C NMR urinary spectrum, including the C5β resonance. The C5β carbon of glucuronate, like that of gluconate C2 and phenylacetylglutamine C2, has differing coupling constants with its nearest neighboring carbons ($J_{C5-C6}$=59 Hz and $J_{C5-C4}$=40 Hz) and, hence appears also as nine resolved resonances. The relative areas of the gluconate C2, glucuronate C5β, and glutamine C2 multiplets are compared in Table 3.

The multiplet areas of glucuronate C5β will be identical to those of gluconate C2 (from blood) if the distribution of $^{13}$C isotopomers is identical in glyceraldehyde-3-phosphate (triose unit reflected by gluconate C2) and dihydroxyacetone phosphate (triose unit reflected by glucuronate C5β). Since both species originate from PEP with no rearrangement of the carbon skeleton, their labeling patterns should be identical, assuming negligible pentose cycle activity (3). However, the fractional enrichments of the two pools can differ as a result of a) incomplete equilibration of the label by triose phosphate isomerase and b) influx of unlabeled glycerol into the dihydroxyacetone phosphate pool. Both of these effects dilute the $^{13}$C-enrichment of dihydroxyacetone phosphate relative to glyceraldehyde-3-phosphate, hence carbons 4, 5 and 6 of glucose-6-phosphate will be more enriched than carbons 1, 2 and 3. Within both glucuronate and gluconate, carbons 4, 5 and 6 had a slight, but systematic elevation of $^{13}$C-enrichment compared to the corresponding carbons 1, 2 and 3, consistent with a small dilution from this source.

Significant excesses in labeling of the bottom half vs the top half of plasma glucose following infusion of $^{14}$C-lactate have been reported in fed humans, but both halves were equally labeled after 60 hours of fasting (Magnusson et. al. 1990). Our observations fall in between these two extremes, consistent with the intermediate 24-hour fasting period used in our study.

The $^{13}$C NMR spectra of urine samples from three subjects featured weak multiplet signals at 58 and 39 ppm which, on the basis of chemical shifts and coupling constants have been tentatively assigned to carbons 2 and 3 of [U-$^{13}$C] 3-hydroxypropionate. The C1 carboxyl resonance of this metabolite was obscured by numerous multiply-labeled and natural abundance carboxyl resonances which occupy a crowded region of the $^{13}$C NMR spectrum. [U-$^{13}$C]3-hydroxypropionate is the terminal β-oxidation product of [U-$^{13}$C]propionyl-CoA and its formation has been associated with saturation of the propionyl-CoA carboxylase pathway (Ando et. al. 1972). The fact that only the uniformly-labeled isotopomer was observed indicates that the carbon skeleton of [U-$^{13}$C]propionate was intact when it entered the hepatic [U-$^{13}$C]propionyl-CoA pool.

Values for anaplerotic inflow (y), recycling of OAA carbons via pyruvate (pk) and gluconeogenic flux (g) were determined from gluconate $^{13}$C spectra obtained from the 120, 150, and 180 minute blood samples and from the glucuronate and phenylacetylglutamine $^{13}$C spectra obtained from the 2, 3, and 4 hour urine samples according to the method of the invention. The gluconate C2, glucuronate C5β and phenylacetylglutamine C2 multiplet areas (Table 3) were substituted into equations previously presented to give estimates of y, pk and g (Table 3).

Table 3 shows multiplet areas from the $^{13}$C NMR spectra of gluconate C2, glucuronate C5β and phenylacetylglutamine C2 for six normal individuals following a 24-hour fast. For gluconate, the mean and standard deviation for the 120, 150 and 180 minute blood samples is shown for each individual. For glucuronate and phenylacetylglutamine, the mean and standard deviation for the 2–3 hour and 3–4 hour urine samples is shown for each individual. Multiplet nomenclature is the same as that used in FIG. 8.

TABLE 3

| Subject | Gluconate C2 | | Glucuronate C5β | | Phenylacetyl-glutamine C2 | |
|---|---|---|---|---|---|---|
| ML | S | 0.289 ± 0.024 | S | 0.262 ± 0.026 | S | 0.396 ± 0.032 |
|  | D12 | 0.419 ± 0.002 | D56 | 0.445 ± 0.004 | D23 | 0.374 ± 0.011 |
|  | D23 | 0.056 ± 0.001 | D45 | 0.060 ± 0.008 | D12 | 0.060 ± 0.008 |
|  | Q | 0.237 ± 0.023 | Q | 0.234 ± 0.023 | Q | 0.161 ± 0.016 |
| GA[1] | S | 0.260 ± 0.032 | S | 0.353 ± 0.004 | S | 0.469 ± 0.062 |
|  | D12 | 0.420 ± 0.039 | D56 | 0.409 ± 0.016 | D23 | 0.358 ± 0.063 |

TABLE 3-continued

| Subject | Gluconate C2 | | Glucuronate C5β | | Phenylacetyl-glutamine C2 | |
|---|---|---|---|---|---|---|
|  | D23 | 0.059 ± 0.008 | D45 | 0.053 ± 0.011 | D12 | 0.050 ± 0.001 |
|  | Q | 0.244 ± 0.017 | Q | 0.163 ± 0.032 | Q | 0.124 ± 0.001 |
| DE | S | 0.336 ± 0.030 | S | 0.343 ± 0.035 | S | 0.513 ± 0.039 |
|  | D12 | 0.390 ± 0.018 | D56 | 0.428 ± 0.001 | D23 | 0.345 ± 0.031 |
|  | D23 | 0.072 ± 0.016 | D45 | 0.051 ± 0.011 | D12 | 0.047 ± 0.004 |
|  | Q | 0.202 ± 0.008 | Q | 0.178 ± 0.008 | Q | 0.116 ± 0.020 |
| MW | S | 0.322 ± 0.063 | S | 0.217 ± 0.031 | S | 0.527 ± 0.069 |
|  | D12 | 0.403 ± 0.027 | D56 | 0.432 ± 0.024 | D23 | 0.317 ± 0.034 |
|  | D23 | 0.068 ± 0.009 | D45 | 0.067 ± 0.010 | D12 | 0.043 ± 0.008 |
|  | Q | 0.205 ± 0.040 | Q | 0.284 ± 0.003 | Q | 0.113 ± 0.028 |
| SH[2] | S | 0.338 ± 0.041 | S | 0.251 | S | 0.389 |
|  | D12 | 0.429 ± 0.034 | D56 | 0.465 | D23 | 0.476 |
|  | D23 | 0.058 ± 0.005 | D45 | 0.086 | D12 | 0.041 |
|  | Q | 0.175 ± 0.015 | Q | 0.198 | Q | 0.094 |
| JJ | S | 0.478 ± 0.047 |  | No Data Available | S | 0.567 ± 0.062 |
|  | D12 | 0.350 ± 0.034 |  | No Data Available | D23 | 0.330 ± 0.030 |
|  | D23 | 0.043 ± 0.001 |  | No Data Available | D12 | 0.036 ± 0.015 |
|  | Q | 0.129 ± 0.011 |  | No Data Available | Q | 0.069 ± 0.016 |

[1]Glucuronate multiplets means and standard deviations were obtained from the 1–2 hour and 2–3 hour urine spectra.
[2]Glucuronate and phenylacetylglutamine multiplets obtained from a single urine collection (2–4 hours). Gluconate multiplet means were obtained only from the 120 minute and 180 minute blood collections.

For all three metabolites, total anaplerotic flux relative to citrate synthase was estimated at 6.0–7.0. However, the phenylacetylglutamine analysis reported a significantly higher OAA-pyruvate recycling flux compared to either glucose and glucuronate, and this resulted in a significantly lower estimate of net gluconeogenesis compared to the hexose analyses (1.4 vs 2.4). These data parallel results wherein net gluconeogenic fluxes reported by glucose and phenylacetylglutamine following infusion of $^{14}$C-propionate were ~3.0 and ~1.8, respectively (Landau et al., 1993). With the exception of one individual, the multiplet ratios of glucuronate C5β and gluconate C2 were similar, providing consistent values for y, pk and g (see Table 2). This indicates that both triose components of the parent hepatic glucose-6-phosphate molecule had similar $^{13}$C isotopomer distributions.

Table 4 shows estimations of total anaplerosis (y), oxaloacetate-pyruvate recycling (pk) and net anaplerotic outflow (g) from the $^{13}$C multiplets of gluconate, glucuronate and phenylacetylglutamine from 24-hour fasted human subjects.

TABLE 4

| | Gluconate C2 | | | Glucuronate C5β | | | Phenylacetylglutamine C2 | | |
|---|---|---|---|---|---|---|---|---|---|
| Subject | y | pk | g | y | pk | g | y | pk | g |
| ML | 6.48 | 3.25 | 3.23 | 6.42 | 3.45 | 2.97 | 5.23 | 3.55 | 1.68 |
| GA | 6.12 | 2.98 | 3.14 | 6.72 | 4.64 | 2.08 | 6.16 | 4.68 | 1.48 |
| DE | 4.42 | 2.61 | 1.81 | 7.39 | 4.90 | 2.49 | 6.34 | 4.87 | 1.47 |
| MW | 4.93 | 2.91 | 2.02 | 5.45 | 2.21 | 3.24 | 6.37 | 4.74 | 1.63 |
| SH | 6.40 | 4.38 | 2.02 | 4.41 | 3.10 | 1.31 | 10.60 | 9.32 | 1.28 |
| JJ | 7.14 | 5.14 | 2.00 | No Data Available | | | 8.16 | 7.25 | 0.91 |
| Mean | 5.92 | 3.55[a] | 2.37[c] | 6.08 | 3.66[a] | 2.42[c] | 7.14 | 5.74[b] | 1.41[d] |
| (S.D.) | (1.03) | (0.99) | (0.64) | (1.16) | (1.11) | (0.76) | (1.94) | (2.13) | (0.28) |

[a] and [b] are significantly different from each other ($p < 0.05$)
[c] and [d] are significantly different from each other ($p < 0.01$)

The anaplerotic flux (y) determined here is slightly lower (6.0 vs. 7.0) than reported elsewhere while pyruvate-oxaloacetate recycling (pk) flux was similar (~3.6 vs. 3.7). (Magnusson et al., 1990). While estimates of pk may be inflated by flux from the Cori cycle (Id., Katz et. al., 1993), the study protocol was designed to minimize any contribution from extrahepatic pathways. The Cori cycle has been estimated to maximally contribute about 15% to the total hepatic glucose output in starved rats (Id.). Any lactate generated in extrahepatic tissues from $^{13}$C-enriched glucose and returned to the liver via the Cori cycle would supplement estimates of intrahepatic pyruvate-oxaloacetate recycling. Assuming steady-state conditions and no glycogenolysis, a 15% Cori cycle contribution would result in a 15% underestimation of g while pk will be correspondingly increased (y being unchanged). The effects of this level of Cori cycling on pk is rather modest; 15% of g amounts to 0.36 units, or about 10% of our pk estimate. However, it has been estimated that about one-third of the total hepatic glucose output is derived from glycogenolysis (Landau et. al., 1996) after a 24 hour fast, so dilution of blood glucose with unlabeled glucose via glycogenolysis would further attenuate the 10% over estimate of pk to about 3%. The bulk of the observed pk flux activity detected in this study appears to originate from hepatic metabolism.

The estimate of net gluconeogenic flux was somewhat lower than previously reported values (~2.4 vs. 3.3), perhaps entirely due to the length of the fasting period in the two studies (24 hr. vs. 60 hr.). (Magnusson et al., 1990). It has been shown that 3-carbon gluconeogenic sources contribute 67% of the total hepatic glucose output after a 22 hr fasting period, but over 90% after a 42 hr fasting period (Landau et. al., 1996). This increased demand for 3-carbon precursors would be expected to be fulfilled in part by an increased gluconeogenic flux from the citric acid cycle.

REFERENCES

The following literature citations as well as those cited above are incorporated in pertinent part by reference herein for the reasons cited in the above text:

Abraham, Fisher, Loftus, In: *Introduction to NMR Spectroscopy*, J. Wiley, New York, p. 73, 1988.
Ando, Rasmussen, Nyham, Hull, *Proc. Natl. Acad. Sci.*, 69:2807–2811, 1972.
Bergmeyer, Bernt, Schmidt, Stork, In: *Methods of Enzymatic Analysis*, 3:1196–1201, Academic Press, Inc. London, 1974.
Beylot, Previs, David, Brunengraber, *Anal. Biochem.*, 212:526–531, 1993.
Blair, Cook, Lardy, *J. Biol. Chem.*, 248:3608–3614, 1973.
Brass, *J. Nutr.*, 122:234–240, 1992.
Chan, Freedland, *Biochem. J*, 127:539–543, 1972.
Clark, Rognstad, Katz, *Biochem. Biophys. Res. Commun.*, 54:1141–1148, 1973.
Cline, Rothman, Magnusson, Katz, Shulman, *J Clin. Invest.*, 94:2369–2376, 1994.
Cohen, *Biochemistry*, 26:573–580, 1987.
Cohen, Glynn, Shulman. *Proc. Natl. Acad. Sci.*, 78:60–64, 1981.
Cohen, *J Biol. Chem.*, 256:3428–3432, 1981.
Corkey et al., *J Biol. Chem.*, 257:9668–9675, 1991.
Cummings, Pomare, Branch, Naylor, Macfarlane, *Gut.*, 28:1221–1227, 1987.
Dankert, Zijlstra Wolthers, *Clin. Chim. Acta.*, 110:301–307, 1981.
Des Rosiers, DiDonato, Comte, Laplante, Marcoux, David, Fenandez, Brunengraber, *J. Biol. Chem.*, 270:10027–10036, 1995.
DiDonato, Des Rosiers, Montgomery, David, Garneau, Brunengraber, *J. Biol. Chem.*, 268:4170–4180, 1993.
Doi, Inoue, Kogire, Sumi, Takaori, Suzuki, Tobe, *Nippon. Geka. Gakkai. Zasshi.*, 89:560–567, 1988.
Dugelay, Yang, Soloviev, Previs, Agarwal, Fernandez, Brunengraber, *Anal. Biochem.*, 221:368–373, 1994.
Ekberg, Chandramouli, Kumaran, Schumann, Wahren, Landau, *J. Biol. Chem.*, 270:21715–21717, 1995.
Fafournoux, Remesy, Demigne, *Biochem. Biophys. Acta*, 818:73–80, 1985.
Friedman, Goodman, Saunders, Kostos, Weinhouse, *Arch. Bioch. Biophys.*, 143:566–578, 1971.
Grunnet and Katz, *Biochem. J.*, 172:595–603, 1978.
Gruetter, Novotny, Boulware, Rothman, Mason, Shulman, Shulman, Tamborlane, *Proc. Natl. Acad. Sci. USA*, 89:1109–1112, 1992.
Gruetter, Novotny, Boulware, Mason, Rothman, Shulman, Prichard, and Shulman, *J Neurochem.*, 63:1377–1385, 1994.
Jeffrey et al., *Am. J. Physiol.*, 271:35–46, 1996.
Jeffrey, Storey, Sherry, Malloy, *Am J. Physiol.*, 271:E788–E799, 1996.
Jones and Titheradge, *Arch. Biochem. Biophys.*, 326:202–206, 1996.
Jones, Cottam, Miller, Sherry, Malloy, *Anal. Bioch.*, 217:148–152, 1994.
Jones et al., *FEBS Lett.*, 412:131–137, 1997.
Jungermann, et. al., *Eur. J. Biochem.*, 123:429–436, 1982.
Jungermann et. al., *Naturwissenschaften*, 72:76–84, 1985.
Jungermann et. al., *Diabetes. Metab. Rev.*, 3:269–293, 1987.
Jungermann et.al., *Physiol. Rev.*, 69:708–764, 1989.
Katz and Lee, *PNAS*, 88:2103–2107,1991.
Katz, *Am. J. Physiol.*, 248:R391–R399, 1985.
Katz, Wals, Lee, *J. Biol. Chem.*, 268:25509–25521, 1993.

Landau et al., *J. Biol. Chem.*, 266:6975–6984, 1991.
Landau et. al., *Am. J. Physiol.*, 265:E636–E647, 1993.
Landau et. al., *J. Clin. Invest.*, 98:378–385, 1996.
Lapidot and Gopher, *J. Biol. Chem.*, 269:27198–27208, 1994.
Laurent et. al., *European. J. Clin. Nutr.*, 49:484–491, 1995.
Magnusson et. al., *Proc. Natl. Acad. Sci. USA*, 85:4682–4685, 1988.
Magnusson et. al., *J. Biol. Chem.*, 266:6975–6984, 1990.
Malloy et al., *MAGMA*, 4:35–46, 1996.
Malloy, Sherry, Jeffrey, *Am. J. Physiol.*, 259:H987–H995, 1990.
Malloy, Sherry, Jeffrey, *J. Biol. Chem.*, 263:6964–6971, 1988.
Malloy et. al., *FEBS. Lett.*, 212:58–62, 1987.
Matsuishi, Stumpf, Seliem, Eguren, Chrislip, *Biochem. Med. Metab. Biol.*, 45:244–253, 1991.
Patel, DeBuysere, Olson, *Arch. Biochem. Biophys.*, 220:405–414, 1983.
Petersen et al., *Am. J. Physiol.*, 267:E273–E277, 1994.
Petersen, Cline, Blair, Shulman, *Am. J. Physiol.*, 267:E273–E277, 1994.
Press, Flannery, Teukolsky, and Vetterling, In: *Numerical recipes in C. The Art of Scientific Computing*, Cambridge University Press, pp 255–289, 1988.
Remesy, Demigne, *Ann. Nutr. Metab.*, 27:57–70, 1983.
Rothman, Novotny, Shulman, Howseman, Petroff, Mason, Nixon, Hanstock, Prichard, Shulman, *Proc. Natl. Acad. Sci. USA*, 89:9603–9606, 1992
Seglen, *Methods Cell Biol.*, 13:29–83, 1976.
Sherry et. al., *Biochem. J.* 254:593–598, 1988.
Sherry et. al., *Biochemistry*, 33:6268–6275, 1994.
Sherry and Malloy, *Cell Biochem. Func.*, 14:259–268, 1996.
Strisower, Kohler, Chaikoff, 1952 *J. Biol. Chem.*, 198:115–126, 1952.
Szczepaniak et. al., *Magn. Reson. Med.*, 36:451–457, 1996.
Tayek and Katz, *Amer. J. Physiol.*, 270:E709–E717, 1996.
Topping, Illman, Taylor, McIntosh, *Ann. Nutr. Metab.*, 29:325–331, 1985.
Wimmer et. al., *Histochemistry*, 64:23–33, 1989.

What is claimed is:

1. A method for determining relative pyruvate cycling flux in a mammal, comprising:
   a) administering $(1,2,3-{}^{13}C_3)$ propionate, $(1,2,3-{}^{13}C_3)$ lactate, $(1,2,3-{}^{13}C_3)$ pyruvate, or $(1,2,3-{}^{13}C_3)$ alanine to said mammal;
   b) obtaining a blood sample from said mammal; and
   c) determining a relative rate of pyruvate cycling from a $^{13}C$ NMR spectrum of $^{13}C$-labeled glutamate or gluconate in said sample,
   wherein the relative pyruvate cycling flux is calculated from the ratio of area under selected $[^{13}]C2$ peaks of glutamate or gluconate.

2. The method of claim 1 wherein the relative rate of pyruvate cycling flux is determined from the D12, D23, and Q $[^{13}]C2$ glutamate peak areas shown in FIG. 2 according to the expression (D23–Q)/D12.

3. The method of claim 1 wherein the relative rate of pyruvate cycling flux is determined from the $[^{13}]C2$ gluconate peak areas D12, D23 and Q shown in FIG. 2 according to the expression (D12–Q)/D23.

4. The method of claim 1 wherein relative rate of pyruvate cycling flux is calculated as follows:
   a) proton-decoupling the $^{13}C$ NMR spectrum;
   b) identifying the $[^{13}]C2$ glutamate resonance peaks comprising a quartet, two doublets and a singlet; and
   c) obtaining a relative rate of pyruvate cycling flux from the areas under said resonance peaks from the relationship (D23–Q)/D12 where D23 is the area of doublet D23, Q is the area of quartet Q, and D12 is the area of doublet D12 as shown in FIG. 2 in the C2 glutamate NMR spectrum centered about a shift of 55.2 ppm.

5. The method of claim 1 wherein relative rate of pyruvate cycling flux is calculated as follows:
   a) proton-decoupling the $^{13}C$ NMR spectrum;
   b) identifying the $[^{13}]C2$ gluconate resonance peaks comprising a quartet, two doublets and a singlet; and
   c) obtaining a relative rate of pyruvate cycling flux from the areas under said resonance peaks from the relationship (D12–Q)/D23 where D23 is the area of doublet D23, D12 is the area of doublet D12, and Q is the area of quartet Q as shown in FIG. 2 in the C2 gluconate NMR spectrum centered about a shift of 75.9 ppm.

6. A method of determining an amount of glucose production, comprising:
   a) administering to a mammal $(1,2,3\ {}^{13}C_3)$ propionate;
   b) infusing said mammal with $(1,6\ {}^{13}C_2)$ glucose at a defined rate;
   c) obtaining a ratio of peak areas S/D from the $^{13}C$ NMR proton decoupled spectrum of glucose or gluconate from the peaks shown in FIG. 4 where S is a singlet and D is doublet 16;
   d) obtaining $^{13}C$ enrichments of glucose by proton NMR; and
   e) determining the amount of glucose production wherein the amount of glucose production is determined by multiplying the amount of glucose infused into said mammal in step b) by the ratio of peak areas S/D as determined in step c), by the $^{13}C$ enrichment determined in step D.

7. A method for determining the relative rate of anaplerosis in a mammal, comprising:
   a) administering $(1,2,3-{}^{13}C_3)$ propionate, $(1,2,3-{}^{13}C_3)$ lactate, $(1,2,3-{}^{13}C_3)$ pyruvate, or $(1,2,3-{}^{13}C_3)$ alanine to said mammal;
   b) obtaining a blood sample from said mammal; and
   c) determining a relative rate of anaplerosis from a $^{13}C$ NMR spectrum of $^{13}C$-labeled glutamate or gluconate in said sample,
   wherein the relative rate of anaplerosis is calculated from the ratio of area under selected $[^{13}]C2$ peaks of glutamate or gluconate.

8. The method of claim 7 wherein the relative rate of anaplerosis is determined from the $[^{13}]C2$ glutamate peak areas D12 and D23 shown in FIG. 2 according to the expression (D23–D12)/D12.

9. The method of claim 7 wherein the relative rate of anaplerosis is determined from the $[^{13}]C2$ gluconate peak areas D12 and D23 shown in FIG. 2 according to the expression (D12–D23)/D23.

10. The method of claim 7 wherein relative rate of anaplerosis is calculated as follows:
   a) proton-decoupling the $^{13}C$ NMR spectrum;
   b) identifying the $[^{13}]C2$ glutamate resonance peaks comprising a quartet, two doublets and a singlet; and
   c) obtaining a relative rate of anaplerosis from the areas under said resonance peaks from the relationship (D23–D12)/D12 where D23 is the area of doublet D23, and D12 is the area of doublet D12 as shown in FIG. 2 in the C2 glutamate NMR spectrum centered about a shift of 55.2 ppm.

11. The method of claim 7 wherein relative rate of anaplerosis is calculated as follows:
   a) proton-decoupling the $^{13}$C NMR spectrum;
   b) identifying the [$^{13}$]C2 gluconate resonance peaks comprising a quartet, two doublets and a singlet; and
   c) obtaining a relative rate of anaplerosis from the areas under said resonance peaks from the relationship (D12–D23)/D23 where D23 is the area of doublet D23, and D12 is the area of doublet D12 as shown in FIG. 2 in the C2 gluconate NMR spectrum centered about a shift of 75.9 ppm.

12. A method for determining relative glucose production in a mammal, comprising:
   a) administering (1,2,3-$^{13}$C$_3$) propionate, (1,2,3-$^{13}$C$_3$) lactate, (1,2,3-$^{13}$C$_3$) pyruvate, or (1,2,3-$^{13}$C$_3$) alanine to said mammal;
   b) obtaining a blood sample from said mammal; and
   c) determining a relative rate of glucose production from a $^{13}$C NMR spectrum of $^{13}$C-labeled glutamate or gluconate in said sample,
   wherein the relative rate of glucose production is calculated from the ratio of area under selected [$^{13}$]C2 peaks of glutamate or gluconate.

13. The method of claim 12 wherein the relative rate of glucose production is determined from the [$^{13}$]C2 glutamate peak areas D12 and Q shown in FIG. 2 according to the expression (Q–D12)/(2×D12).

14. The method of claim 12 wherein the relative rate of glucose production is determined from the [$^{13}$]C2 gluconate peak areas D23 and Q shown in FIG. 2 according to the expression (Q–D23)/(2×D23).

15. The method of claim 12 wherein relative rate of glucose production is calculated as follows:
   a) proton-decoupling the $^{13}$C NMR spectrum;
   b) identifying the [$^{13}$]C2 glutamate resonance peaks comprising a quartet, two doublets and a singlet; and
   c) obtaining a relative rate of glucose production from the areas under said resonance peaks from the relationship (Q–D12)/(2×D12) where Q is the area of quartet Q, and D12 is the area of doublet D12 as shown in FIG. 2 in the C2 glutamate NMR spectrum centered about a shift of 55.2 ppm.

16. The method of claim 12 wherein relative rate of glucose production is calculated as follows:
   a) proton-decoupling the $^{13}$C NMR spectrum;
   b) identifying the [$^{13}$]C2 gluconate resonance peaks comprising a quartet, two doublets and a singlet; and
   c) obtaining a relative rate of glucose production from the areas under said resonance peaks from the relationship (Q–D23)/(2×D23) where Q is the area of quartet Q, and D23 is the area of doublet D23 as shown in FIG. 2 in the C2 gluconate NMR spectrum centered about a shift of 75.9 ppm.

17. A method for determining relative pyruvate cycling flux in a mammal, comprising:
   a) administering (1,2,3-$^{13}$C$_3$) propionate, (1,2,3-$^{13}$C$_3$) lactate, (1.2,3-$^{13}$C$_3$) pyruvate, or (1,2,3-$^{13}$C$_3$) alanine to said mammal;
   b) obtaining a urine sample from said mammal;
   c) administering a compound metabolizable to a glucuronate or a glutamine;
   d) determining a relative rate of pyruvate cycling from a $^{13}$C NMR spectrum of said $^{13}$C-labeled glucuronate or glutamine in said sample;
   wherein the relative pyruvate cycling flux is calculated from the ratio of area under selected [$^{13}$]C NMR peaks of said glucuronate or glutamine.

18. The method of claim 17 wherein the compound administered is acetaminophen or phenylacetate.

19. The method of claim 18 wherein the relative rate of pyruvate cycling flux is determined from the [$^{13}$]C2 phenylacetylglutamine peak areas D12, D23 and Q shown in FIG. 8 according to the expression (D23–Q)/D12.

20. The method of claim 18 wherein the relative rate of pyruvate cycling flux is determined from the [$^{13}$]C5β glucuronate peak areas D45, D56 and Q shown in FIG. 8 according to the expression (D56–Q)/D45.

21. A method for determining the relative rate of anaplerosis in a mammal, comprising:
   a) administering (1,2,3-$^{13}$C$_3$) propionate, (1,2,3-$^{13}$C$_3$) lactate, (1,2,3-$^{13}$C$_3$) pyruvate, or (1,2,3-$^{13}$C$_3$) alanine to said mammal;
   b) obtaining a urine sample from said mammal;
   c) administering a compound metabolizable to a glucuronate or a glutamine;
   d) determining a relative rate of pyruvate cycling from a $^{13}$C NMR spectrum of said $^{13}$C-labeled glucuronate or glutamine in said sample;
   wherein the relative pyruvate cycling flux is calculated from the ratio of area under selected [$^{13}$]C NMR peaks of said glucuronate or glutamine.

22. The method of claim 21 wherein the compound administered is acetaminophen or phenylacetate.

23. The method of claim 22 wherein the relative rate of anaplerosis is determined from the [$^{13}$]C2 phenylacetylglutamine peak areas D12 and D23 shown in FIG. 8 according to the expression (D23–D12)/D12.

24. The method of claim 22 wherein the relative rate of anaplerosis is determined from the [$^{13}$]C5β glucuronate peak areas D45 and D56 shown in FIG. 8 according to the expression (D56–D45)/D45.

25. A method for determining relative glucose production in a mammal, comprising:
   a) administering (1,2,3-$^{13}$C$_3$) propionate, (1,2,3-$^{13}$C$_3$) lactate, (1,2,3-$^{13}$C$_3$) pyruvate, or (1,2,3-$^{13}$C$_3$) alanine to said mammal;
   b) obtaining a urine sample from said mammal;
   c) administering a compound metabolizable to a glucuronate or a glutamine;
   d) determining a relative rate of pyruvate cycling from a $^{13}$C NMR spectrum of said $^{13}$C-labeled glucuronate or glutamine in said sample;
   wherein the relative pyruvate cycling flux is calculated from the ratio of area under selected [$^{13}$]C2 NMR peaks of said glucuronate or glutamine.

26. The method of claim 25 wherein the compound administered is acetaminophen or phenylacetate.

27. The method of claim 26 wherein the relative rate of glucose production is determined from the [$^{13}$]C2 phenylacetylglutamine peak areas D12 and Q shown in FIG. 8 according to the expression (Q–D12)/(2×D12).

28. The method of claim 26 wherein the relative rate of glucose production is determined from the [$^{13}$]C5β glucuronate peak areas D45 and Q shown in FIG. 8 according to the expression (Q–D45)/(2×D45).

29. The method of claim 1 or claim 7 or claim 12 or claim 17 or claim 21 or claim 25 wherein (1,2,3 $^{13}$C$_3$) propionate is administered to said mammal.

30. The method of claim 1 or claim 7 or claim 12 or claim 17 or claim 21 or claim 25 wherein the (1,2,3 $^{13}$C$_3$) propionate is administered orally or intravenously.

31. The method of claim 1 or claim 7 or claim 12 or claim 17 or claim 21 or claim 25 wherein the mammal is human.

* * * * *